(12) United States Patent
Elmaleh et al.

(10) Patent No.: US 7,785,618 B2
(45) Date of Patent: Aug. 31, 2010

(54) CONJUGATES COMPRISING A BIODEGRADABLE POLYMER AND USES THEREFOR

(76) Inventors: David R. Elmaleh, 38 Hartman Rd., Newton, MA (US) 02159; Simon C. Robson, 250 Glen Rd., Weston, MA (US) 02493; Mikhail L. Papisov, 60 Woodside Rd., Winchester, MA (US) 01890

( * ) Notice: Subject to any disclaimer, the term of this patent is extended or adjusted under 35 U.S.C. 154(b) by 500 days.

(21) Appl. No.: 10/922,378

(22) Filed: Aug. 20, 2004

(65) Prior Publication Data

US 2005/0169968 A1    Aug. 4, 2005

Related U.S. Application Data

(63) Continuation of application No. PCT/US03/04845, filed on Feb. 19, 2003.

(60) Provisional application No. 60/358,303, filed on Feb. 20, 2002.

(51) Int. Cl.
*A61F 2/00* (2006.01)
(52) U.S. Cl. .................. 424/426; 424/94.6
(58) Field of Classification Search .............. None
See application file for complete search history.

(56) References Cited

U.S. PATENT DOCUMENTS

| | | | |
|---|---|---|---|
| 4,729,956 A | 3/1988 | Hopkins | 435/188 |
| 5,221,495 A | 6/1993 | Cao et al. | 510/321 |
| 5,240,843 A | 8/1993 | Gibson et al. | 435/188 |
| 5,582,172 A | 12/1996 | Papisov et al. | 128/653.4 |
| 5,811,510 A | 9/1998 | Papisov | 528/230 |
| 5,863,990 A | 1/1999 | Papisov | 525/398 |
| 5,958,398 A | 9/1999 | Papisov | 424/78.08 |
| 6,822,086 B1 | 11/2004 | Papisov | 536/24.2 |
| 2004/0105840 A1 | 6/2004 | Kinstler et al. | 424/78.37 |

FOREIGN PATENT DOCUMENTS

| | | |
|---|---|---|
| EP | 0451924 | 10/1991 |
| GB | 1512651 A | 6/1978 |
| JP | 3158758 * | 7/1991 |
| SU | 761477 | 9/1980 |
| WO | WO-93/25212 A1 | 12/1993 |
| WO | WO 9632419 A1 * | 10/1996 |
| WO | WO 96/40792 | 12/1996 |
| WO | WO0023459 A1 * | 4/2000 |

OTHER PUBLICATIONS

Drago et al., Enzyme Stability and Stabilisation: Applications and Case Studies, Focus on Biotechnology, *Engineering and Manufacturing for Biotechnology*, pp. 361-376 (2001).
Kaczmarek et al., Identification and Characterization of CD39/Vascular ATP Diphosphohydrolase, *Journal of Biological Chemistry*, 271 (51): 33116-33122 (1996).
International Search Report (PCT/US03/04845).
Supplemental European Search Report (EP 03716070).
Epton, R. et al., "Water-Insolubilisation of Glycoside Hydrolases with Cross-Linked Poly(Acryloylaminoacetaldehydedimethyl Acetal) (Enzacryl Polyacetal)", *Carbohydrate Research*, 22(2):301-306 (Elsevier Publishing, Amsterdam, NL, May 1, 1972).
Matsutani, S. et al., "Studies on the Mechanism of Hypergammaglobulinemia, in Particular an Increase of Serum IgA in Chronic Liver Diseases—From the Aspect of the Antibody Production against Extrinsic Antigens"; *Sapporo Medical Journal*, 51(4):301-318 (May 31, 1982).
Rao, P. N. et al., "Synthesis of New Steriod Haptens for Radioimmunoassay. Part II. 15β-Carboxyethylmercaptodehydroepaindrosterone Bovine Serum Albumin Conjugate. Specific Antiserum for Solid-Phase Radioimmunoassay of Dehydroepiandrosterone", *Steroids*, 28(1):110-113 (Elsevier Publishing, NY, NY, Jul. 1, 1976).
European Search Report dated Nov. 9, 2009.

* cited by examiner

*Primary Examiner*—Sandra Saucier
*Assistant Examiner*—Satyendra K Singh
(74) *Attorney, Agent, or Firm*—Beth E. Arnold, Esq.; Foley Hoag LLP

(57) ABSTRACT

Biologically active agents covalently linked to a polymer. The polymer is preferably a biodegradable polymer are provided. The biologically active agent is preferably a protein, such as an extracellular soluble protein, e.g., an extracellular enzyme. The enzyme can be an apyrase, e.g., NTPDase. Conjugates of the invention can be used as therapeutics in subjects. For example, a conjugate comprising an apyrase can be used for treating and preventing thrombosis, atherosclerotic plaque complications and vascular disorders.

10 Claims, 3 Drawing Sheets

Figure 1

```
Met Glu Asp Thr Lys Glu Ser Asn Val Lys Thr Phe Cys Ser Lys Asn
1               5                   10                  15
Ile Leu Ala Ile Leu Gly Phe Ser Ser Ile Ile Ala Val Ile Ala Leu
                20                  25                  30
Leu Ala Val Gly Leu Thr Gln Asn Lys Ala Leu Pro Glu Asn Val Lys
            35                  40                  45
Tyr Gly Ile Val Leu Asp Ala Gly Ser Ser His Thr Ser Leu Tyr Ile          ACR1
        50              55                  60
Tyr Lys Trp Pro Ala Glu Lys Glu Asn Asp Thr Gly Val Val His Gln
65                  70                  75                  80
Val Glu Glu Cys Arg Val Lys Gly Pro Gly Ile Ser Lys Phe Val Gln
                85                  90                  95
Lys Val Asn Glu Ile Gly Ile Tyr Leu Thr Asp Cys Met Glu Arg Ala
                100                 105                 110
Arg Glu Val Ile Pro Arg Ser Gln His Gln Glu Thr Pro Val Tyr Leu          ACR2
            115                 120             125
Gly Ala Thr Ala Gly Met Arg Leu Leu Arg Met Glu Ser Glu Glu Leu
        130                 135                 140
Ala Asp Arg Val Leu Asp Val Val Glu Arg Ser Leu Ser Asn Tyr Pro
145             150                 155                 160
Phe Asp Phe Gln Gly Ala Arg Ile Ile Thr Gly Gln Glu Glu Gly Ala          ACR3
                165                 170             175
Tyr Gly Trp Ile Thr Ile Asn Tyr Leu Leu Gly Lys Phe Ser Gln Lys
            180                 185                 190
Thr Arg Trp Phe Ser Ile Val Pro Tyr Glu Thr Asn Asn Gln Glu Thr
                195                 200                 205
Phe Gly Ala Leu Asp Leu Gly Gly Ala Ser Thr Gln Val Thr Phe Val          ACR4
            210             215                 220
Pro Gln Asn Gln Thr Ile Glu Ser Pro Asp Asn Ala Leu Gln Phe Arg
225                 230                 235                 240
Leu Tyr Gly Lys Asp Tyr Asn Val Tyr Thr His Ser Phe Leu Cys Tyr
                245                 250                 255
Gly Lys Asp Gln Ala Leu Trp Gln Lys Leu Ala Lys Asp Ile Gln Val
                260                 265                 270
Ala Ser Asn Glu Ile Leu Arg Asp Pro Cys Phe His Pro Gly Tyr Lys
        275                 280                 285
Lys Val Val Asn Val Ser Asp Leu Tyr Lys Thr Pro Cys Thr Lys Arg
    290                 295                 300
Phe Glu Met Thr Leu Pro Phe Gln Gln Phe Glu Ile Gln Gly Ile Gly
305                 310                 315                 320
Asn Tyr Gln Gln Cys His Gln Ser Ile Leu Glu Leu Phe Asn Thr Ser
                325                 330                 335
Tyr Cys Pro Tyr Ser Gln Cys Ala Phe Asn Gly Ile Phe Leu Pro Pro
            340                 345                 350
Leu Gln Gly Asp Phe Gly Ala Phe Ser Ala Phe Tyr Phe Val Met Lys
        355                 360                 365
Phe Leu Asn Leu Thr Ser Glu Lys Val Ser Gln Glu Lys Val Thr Glu
    370                 375                 380
Met Met Lys Lys Phe Cys Ala Gln Pro Trp Glu Glu Ile Lys Thr Ser
385                 390                 395                 400
Tyr Ala Gly Val Lys Glu Lys Tyr Leu Ser Glu Tyr Cys Phe Ser Gly
                405                 410                 415
Thr Tyr Ile Leu Ser Leu Leu Leu Gln Gly Tyr His Phe Thr Ala Asp
            420                 425                 430
Ser Trp Glu His Ile His Phe Ile Gly Lys Ile Gln Gly Ser Asp Ala        ACR5
        435                 440                 445
Gly Trp Thr Leu Gly Tyr Met Leu Asn Leu Thr Asn Met Ile Pro Ala
    450                 455                 460
Glu Gln Pro Leu Ser Thr Pro Leu Ser His Ser Thr Tyr Val Phe Leu
465                 470                 475                 480
Met Val Leu Phe Ser Leu Val Leu Phe Thr Val Ala Ile Ile Gly Leu
                485                 490                 495
Leu Ile Phe His Lys Pro Ser Tyr Phe Trp Lys Asp Met Val
                500                 505                 510
```

CONJUGATES COMPRISING A BIODEGRADABLE POLYMER AND USES THEREFOR

GOVERNMENT FUNDING

This invention was made with support under Grant Number HL57307 and HL63972, awarded by the National Institutes of Health; the government, therefore, has certain rights in the invention.

BACKGROUND OF THE INVENTION

A major challenge in the area of the parenteral administration of biologically active materials is the development of a controlled delivery device that is small enough for intravenous application and which has a long circulating half-life. Biologically active materials administered in such a controlled fashion into tissue or blood are expected to exhibit decreased toxic side effects compared to when the materials are injected in the form of a solution, and may reduce degradation of sensitive compounds in the plasma.

A number of injectable drug delivery systems have been investigated, including microcapsules, microparticles, liposomes and emulsions. A significant obstacle to the use of these injectable drug delivery materials is the rapid clearance of the materials from the blood stream by the macrophages of the reticuloendothelial system (RES). For example, polystyrene particles as small as sixty nanometers in diameter are cleared from the blood within two to three minutes. Polystyrene particles are also not biodegradable and therefore not therapeutically useful.

Polymers which are degraded by a physical or chemical process in response to contact with body fluid, while implanted or injected, are generally considered to be biodegradable. Biodegradable polymers have been the subject of increasing interest as materials which can be employed to form a wide variety of pharmaceutical preparations and other biomedical products. Examples of medical applications for biodegradable polymers include tablet coatings, plasma substitutes, gels, contact lenses, surgical implants, as ingredients of eyedrops, and as long-lived circulating and targeted drugs.

However, many polymers have hydrophobic domains and, consequently, their biocompatability is limited. Hydrophobic polymers are vulnerable to non-specific interactions with proteins and lipids which also may cause undesirable side effects. In addition, synthetic polymers, such as vinyl, acrylic and methacrylic polymers, which typically have a hydrophobic main chain, do not degrade readily in vivo.

Hydrophilic polymers are common in nature. For example, polysaccharides are naturally-occurring polymers which include hydrolytically-sensitive acetals in their main chain. However, polysaccharides can interact with cell receptors and/or plasma opsonins, and can cause adverse reactions and other non-desirable effects.

In addition, the activity and half-life of biological agents, such as ecto-enzymes, which are introduced into the blood stream is transient, which therefore limits the biological agents' potential application. To achieve effective therapies, repeated large enzyme dosing may be required. This may in turn result in increased toxicity and side effects as an immune response to the extended enzyme introduction.

Therefore, a need exists for a polymer system which overcomes or minimizes the above-referenced problems and is amenable to modification by a biologically active agent wherein the agent is stabilized and released in a timed manner.

SUMMARY OF THE INVENTION

In one embodiment, the invention provides a conjugate comprising a biologically active agent and a polymer. The polymer is preferably a biodegradable polymer. In a preferred embodiment, the polymer is a polyacetal. The polymer or conjugate can be positively or negatively charged. The biologically active agent can be conjugated to the polymer through covalent, ionic or hydrogen bond(s). Alternatively, the biologically active agent is linked to the polymer through a tether, e.g., a derivative of a compound selected from the group consisting of ethylene glycol-bis-succinimidylsuccinate, succinic acid or succinic anhydride, diaminohexane, glyoxlic acid, short chain polyethylene glycol, and glycine.

The polymer can be crosslinked with epibromohydrin or epichlorhydrin to form a gel. Exemplary polymers have a molecular weight between 0.5 and 500 kDa, preferably between 1 and 300 kDa. In a preferred embodiment the biodegradable polyacetal is poly(hydroxymethylethylenehydroxymethylacetal).

In a preferred embodiment, the biologically active agent is a protein, preferably an extracellular protein, even more preferably an enzyme, and most preferably the enzyme is nucleoside triphosphate diphosphohydrolase (NTPDase), e.g., human CD39 or related ectoenzymes. The NTPDase can comprise an amino acid sequence that is at least about 90% identical to SEQ ID NO: 2 and catalyze hydrolysis of NTPs and/or NDPs. In a further embodiment the apyrase comprises the catalytic domain set forth in SEQ ID NO: 2.

The biodegradable polymer may also be selected from the group consisting of polycarbonates, polyanhydrides, polyorthoesters, polyglycolide (PGA), copolymers of glycolide, poly(glycolide-co-caprolactone) (PGA/PCL), glycolide/L-lactide copolymers (PGA/PLLA), lactide/trimethylene carbonate copolymers (PLA/TMC), glycolide/trimethylene carbonate copolymers (PGA/TMC), polylactides (PLA), stereocopolymers of PLA, poly-L-lactide (PLLA), poly-DL-lactide (PDLLA), L-lactide/DL-lactide copolymers, copolymers of PLA, lactide/tetramethylglycolide copolymers, lactide/α-valerolactone copolymers, lactide/ε-caprolactone copolymers, hyaluronic acid and its derivatives, polydepsipeptides, PLA/polyethylene oxide copolymers, unsymmetrical 3,6-substituted poly-1,4-dioxane-2,5-diones, carboxymethyl cellulose (CMC), poly-β-hydroxybutyrate (PHBA), PHBA/bhydroxyvalerate copolymers (PHBA/HVA), poly-p-dioxanone (PDS), poly-a-valerlactone, poly-ε-caprolactone, methacrylate-N-vinyl-pyrrolidone copolymers, polyesteramides, polyesters of oxalic acid, polydihydropyranes, polyalkyl-2-cyanoacrylates, polyurethanes, polypeptides, poly-β-malic acid (PMLA), poly-β-alcanoic acids, polybutylene oxalate, polyethylene adipate, polyethylene carbonate, polybutylene carbonate, and other polyesters containing silyl ethers, acetals or ketals, and alginates.

Conjugates of the invention can be used for treating subjects. For example, conjugates comprising apyrases can be used for treating subjects that may benefit from modulation of circulating levels of nucleotides in the blood. In an illustrative embodiment, the subject to be treated may be a subject suffering from diseases relating to atherosclerotic disease, abnormal platelet aggregation, excessive angiogenesis, and cellular hyperproliferation, e.g., cancer. Transplant subjects, e.g., those with rejection or preservation injury, may also benefit from administration of conjugates comprising apyrases.

Conjugates comprising apyrases can also be used in vitro, e.g., in stored blood, such as to prevent platelet aggregation and/or leukocyte activation in blood; platelet preparation, or leucopheresis product. Thus, for example, conjugates may be added to a sample of blood or cells (e.g., leukocytes) thereof.

At least one advantage of the conjugates comprising apyrases relative to non conjugated apyrases is that the conjugated apyrases have an increased biological activity and extended in vivo half-life. In addition, conjugates comprising apyrases are potentially less toxic sytemically due to the polymeric biodegradation and slow apyrase release.

BRIEF DESCRIPTION OF DRAWINGS

FIG. 1 depicts the amino acid sequence of human CD39 (SEQ ID NO: 2) and the location of ACR domains.

DETAILED DESCRIPTION OF THE INVENTION

Figure 2:
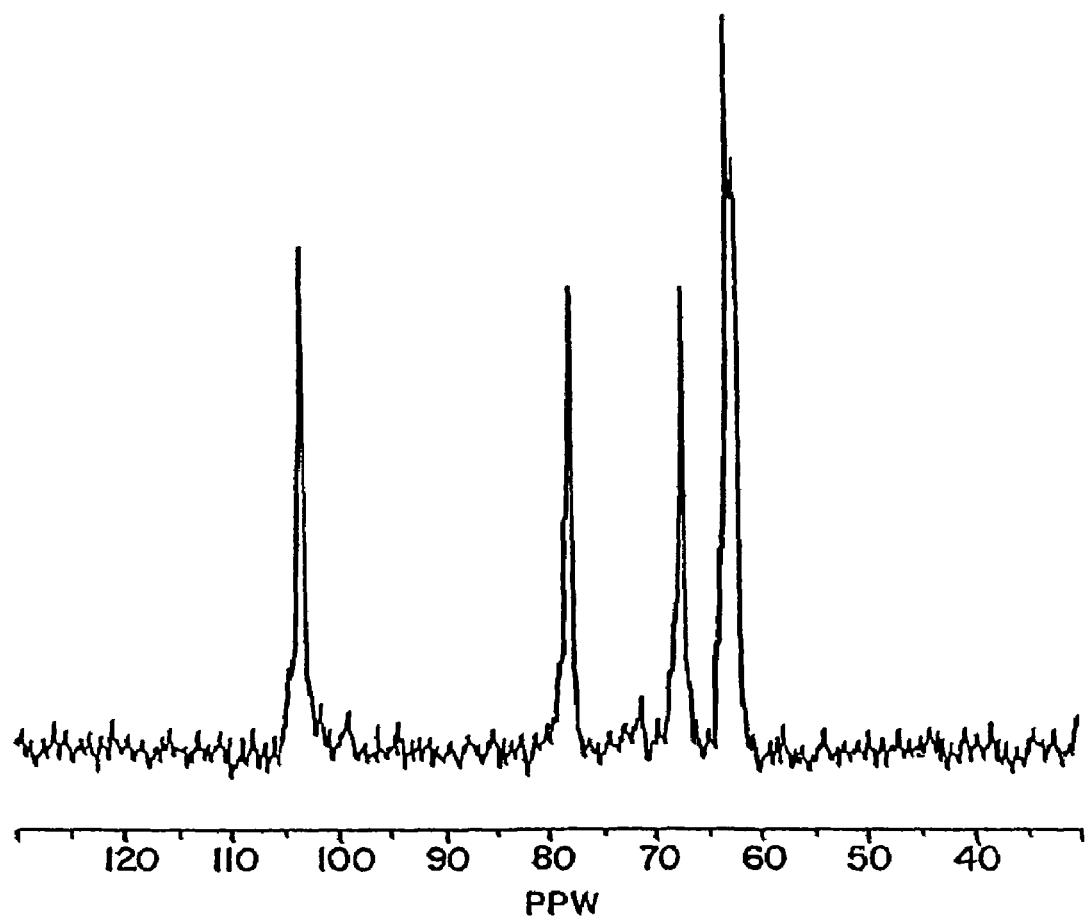
FIG. 2 depicts the $^{13}$C NMR spectrum of a polyacetal used in the biologically active agent conjugates of the current invention dissolved in deuterium oxide.

The features and other details of the invention, either as steps of the invention or as combination of parts of the invention, will now be more particularly described and pointed out in the claims. It will be understood that the particular embodiments of the invention are shown by way of illustration and not as limitations of the invention. The principle features of the invention may be employed in various embodiments without departing from the scope of the invention.

The invention is based at least in part on the discovery that modification of apyrase with a biodegradable polymer, such as Fleximer, provides for stable enzyme activity by several fold. The modification involves in part linking apyrase to the biodegradable polymer.

Definitions

The terms used herein have their usual meaning in the art, however, to even further clarify the present invention, for convenience, the meaning of certain terms and phrases employed in the specification, examples, and appended claims are provided below.

As used herein, the twenty conventional amino acids and their abbreviations follow conventional usage (*Immunology—A Synthesis,* 2nd Edition, E. S. Golub and D. R. Gren, Eds., Sinauer Associates, Sunderland, Mass. (1991), which is incorporated herein by reference). Stereoisomers (e.g., D-amino acids) of the twenty conventional amino acids, unnatural amino acids such as, α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

When referring to an amino acid position as being "about amino acid" it is meant that the amino acid could be up to 10 or preferably 5 amino acids upstream or downstream of the enumerated amino acid.

"Apyrase" refers to an enzyme capable of catalyzing the sequential hydrolysis of nucleoside and deoxynucleotide triphosphate (NTP) to nucleoside diphosphate (NDP) to nucleoside monophosphate (NMP). Nucleoside and deoxynucleoside triphosphates and diphosphates can be, e.g., ATP, ADP, CTP, CDP, GTP, GDP, TTP, TDP, UTP and UDP. The enzyme is also alternately referred to as NTPDase; ADPase; ATPDase; ATPase; ADP monophosphatase and ATP diphosphohydrolase. Exemplary apyrases include CD39 proteins and potato apyrase. The term "apyrase" includes naturally-occurring apyrases, such as those further described herein, as well as fragments and homologs thereof, provided that they have at least one biological activity of an apyrase. For example, an apyrase can be a protein having an amino acid sequence which is at least 70%, preferably at least 80%, more preferably at least 90% (e.g., 95% or greater, e.g. 99% or 100%) identical or similar to SEQ ID NO: 2 or 4 or a protein that is encoded by a nucleic acid that hybridizes to SEQ ID NO: 1 or 3.

"Apyrase conjugate" used interchangeably herein with "apyrase complex" or "modified apyrase" refers to a conjugate or a complex of an apyrase with a polymer. The apyrase and polymer can be linked directly, or indirectly, e.g., through a tether, and can be linked together through a covalent bond or a non covalent bond, e.g., an ionic bond or hydrogen bonds.

"Biocompatible," as that term is used herein, means exhibition of essentially no cytotoxicity while in contact with body fluids. "Biocompatibility" also includes essentially no interactions with recognition proteins, e.g., naturally occurring antibodies, cell proteins, cells and other components of biological systems. However, substances and functional groups specifically intended to cause the above effects, e.g., drugs and prodrugs, are considered to be biocompatible.

"Biodegradable," as that term is used herein, means polymers which are degraded in response to contact with body fluid while implanted or injected in vivo. Examples of biodegradation processes include hydrolysis, enzymatic action, oxidation and reduction. Suitable conditions for hydrolysis, for example, include exposure of the biodegradable polymers to water at a temperature and a pH of circulating blood. Biodegradation of enzyme delivery systems of the present invention can be enhanced in low pH regions of the mammalian body, e.g. an inflamed area.

A "biologically active agent" refers to a molecule or complex having a biological activity. A preferred biologically active agent is a protein having one or more polypeptide chains. A biologically active agent can also be a nucleic acid, e.g., a ribozyme, a polysaccharide, a lipid, derivatives thereof, or a small organic molecule.

"Biological activity of an apyrase" refers to the ability of the apyrase to catalyze the sequential hydrolysis of NTPs or NDPs. The biological activity can be determined, e.g., in an ectonucleotidase or apyrase assay (e.g., ATPase or ADPase assay) or in a biological assay that measures inhibition of platelet aggregation. Exemplary assays are further described herein.

"Conjugated to" in the context of a biologically active agent and a polymer refers to a covalent bond or a non covalent bond, e.g., an ionic interaction or interaction through hydrogen bonds.

"Graft," "transplant" or "implant" are used interchangeably to refer to biological material derived from a donor for transplantation into a recipient, and to the act of placing such biological material in the recipient.

"Host" or "recipient" refers to the body of the patient in whom donor biological material is grafted.

As used herein, the terms "label" or "labeled" refers to incorporation of a detectable marker, e.g., by incorporation of a radiolabeled amino acid or nucleotide or attachment to a polypeptide or nucleic acid of biotinyl moieties that can be detected by marked avidin (e.g., streptavidin containing a fluorescent marker or enzymatic activity that can be detected by optical or colorimetric methods). Various methods of labeling polypeptides, nucleic acids, and glycoproteins are known in the art and may be used. Examples of labels for polypeptides include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

A "patient" or "subject" to be treated by the subject method can mean either a human or non-human animal.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

"Polymeric system" is used interchangeably herein with "polymeric complex" or "conjugate" to refer to a biological agent, e.g., a protein, conjugated to a polymer.

The term "polypeptide having activity of an ATP diphosphohydrolase" includes native ecto-ATP diphosphohydrolase protein, as well as homologs thereof, e.g., oxidation resistant peptide analogs thereof, and soluble truncated forms.

The terms "protein", "polypeptide" and "peptide" are used interchangeably herein when referring to a gene product.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

The phrase "therapeutically-effective amount" as used herein means that amount of a compound, material, or composition comprising a compound of the present invention which is effective for producing some desired therapeutic effect in an animal at a reasonable benefit/risk ratio applicable to any medical treatment.

"Treating" a disease or condition refers to preventing, curing, as well as ameliorating at least one symptom of the condition or disease.

The following definitions pertain to the chemical structure of compounds:

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, J. March, *Advanced Organic Chemistry*, McGraw Hill Book Company, New York, (1977 edition) pp. 251-259. The Hammett constant values are generally negative for electron donating groups (σ[P]=−0.66 for NH$_2$) and positive for electron withdrawing groups (σ[P]=0.78 for a nitro group), σ[P] indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocycle" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, thiazole, thiazolidines, thiazolidin-4-ones, thiazolidin-5-ones, isoxazole, pyridine, pyrazine, pyrimidine, pyridazine, indolizine, isoindole, indole, indazole, purine, quinolizine, isoquinoline, quinoline, tetrahydroquinoline, tetrahydroisoquinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

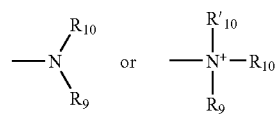

wherein $R_9$, $R_{10}$ and $R'_{10}$ each independently represent a hydrogen permitted by the rules of valence.

The term "acylamino" is art-recognized and refers to a moiety that can be represented by the general formula:

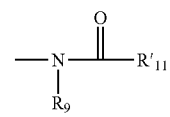

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

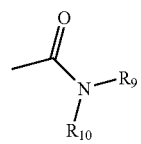

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

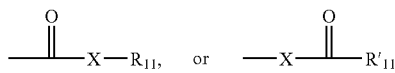

wherein X is a bond or represents an oxygen or a sulfur, and R$_{11}$ represents a hydrogen, an alkyl, an alkenyl, —(CH$_2$)$_m$—R$_8$ or a pharmaceutically acceptable salt, R'$_{11}$ represents a hydrogen, an alkyl, an alkenyl or —(CH$_2$)$_m$—R$_8$, where m and R$_8$ are as defined above. Where X is an oxygen and R$_{11}$ or R'$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiolcarbonyl" group. Where X is a sulfur and R$_{11}$ or R'$_{11}$ is not hydrogen, the formula represents a "thiolester." Where X is a sulfur and R$_{11}$ is hydrogen, the formula represents a "thiolcarboxylic acid." Where X is a sulfur and R$_{11}$' is hydrogen, the formula represents a "thiolformate." On the other hand, where X is a bond, and R$_{11}$ is not hydrogen, the above formula represents a "ketone" group. Where X is a bond, and R$_{11}$ is hydrogen, the above formula represents an "aldehyde" group.

The terms "alkoxyl" or "alkoxy" as used herein refers to an alkyl group, as defined above, having an oxygen attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where m and R$_8$ are described above.

The term "sulfonate" is art recognized and includes a moiety that can be represented by the general formula:

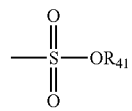

in which R$_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

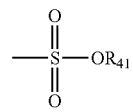

in which R$_{41}$ is as defined above.

The term "sulfonylamino" is art recognized and includes a moiety that can be represented by the general formula:

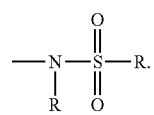

The term "sulfamoyl" is art-recognized and includes a moiety that can be represented by the general formula:

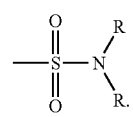

The term "sulfonyl", as used herein, refers to a moiety that can be represented by the general formula:

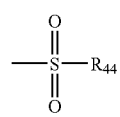

in which R$_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

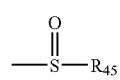

in which R$_{45}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Ilustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2$^{nd}$* ed.; Wiley: New York, 1991).

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Exemplary Polymers

A preferred polymer of the invention is preferably a biodegradable and/or biocompatible polymer, which preferably also contains functionality throughout the backbone chain that can be modified to fonn linkages with the biologically active agents. In an even more preferred embodiment the biodegradable polymer is a polyacetal. The biodegradable biocompatible polyacetals of the present invention have the following chemical structure:

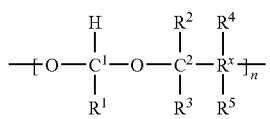

$R^1$ is biocompatible and includes a carbon atom covalently attached to $C^1$. $R^x$ includes a carbon atom covalently attached to $C^2$. "n" is an integer. $R^2$, $R^3$, $R^4$ and $R^5$ are biocompatible and are selected from the group consisting of hydrogen and organic moieties. At least one of $R^1$, $R^2$, $R^3$, $R^4$ and $R^5$ is hydrophilic. Examples of suitable organic moieties are aliphatic groups having a chain of atoms in a range of between about one and twelve atoms.

The term "hydrophilic" as it relates to $R^1$, $R^2$, $R^3$, $R^4$ and $R^5$ denotes organic moieties which contain ionizable, polar, or polarizable atoms, or which otherwise may bind water molecules. Examples of particular hydrophilic organic moieties which are suitable include carbamates, amides, hydroxyls, carboxylic acids and their salts, carboxylic acid esters, amines, sulfonic acids and their salts, sulfonic acid esters, phosphoric acids and their salts, phosphate esters, polyglycol ethers, polyamines, polycarboxylates, polyesters, polythioethers, etc. In preferred embodiments of the present invention, at least one of $R^1$, $R^2$, $R^3$, $R^4$ and $R^5$ include a carboxyl group (COOH), an aldehyde group (CHO) or a methylol (CH$_2$OH). In another preferred embodiment of the present invention, $R^1$, $R^2$, $R^3$, $R^4$ and $R^5$ are methylols. In still another preferred embodiment of the present invention, $R^1$ and $R^2$ are methylols and $R^3$, $R^4$, and $R^5$ are hydrogens.

In yet another embodiment of the present invention, at least one of $R^1$, $R^2$, $R^3$, $R^4$ or $R^5$ is a nitrogen-containing compound. The nitrogen-containing compound can be a drug or a cross-linking agent or a functional group which is suitable as a modifier of biodegradable biocompatible polyacetal behavior in vivo. Examples of such functional groups include antibodies, their fragments, receptor ligands and other compounds that selectively interact with biological systems.

Alternatively, the nitrogen-containing compound can have a chemical structure of —C$_n$H$_{2n}$NR$^6$R$^7$, wherein "n" is an integer. In one embodiment, "n" is one. $R^6$ and $R^7$ can include hydrogen, organic or inorganic substituents. Examples of suitable organic or inorganic groups include aliphatic groups, aromatic groups, complexes of heavy metals, etc.

The biodegradable biocompatible polyacetals of the invention can be cross-linked. A suitable cross-linking agent has the formula X$^1$—(R)—X$^2$, where R is a spacer group and X$^1$ and X$^2$ are reactive groups. Examples of suitable spacer groups include biodegradable or nonbiodegradable groups, for example, aliphatic groups, carbon chains containing biodegradable inserts such as disulfides, esters, etc. The term "reactive group," as it relates to X$^1$ and X$^2$, means functional groups which can be connected by a reaction within the biodegradable biocompatible polyacetals, thereby cross-linking the biodegradable biocompatible polyacetals. Suitable reactive groups which form cross-linked networks with the biodegradable biocompatible polyacetals include epoxides, halides, tosylates, mesylates, carboxylates, aziridines, cyclopropanes, esters, N-oxysuccinimde esters, disulfides, anhydrides etc.

In a preferred embodiment, the biodegradable biocompatible polyacetals are cross-linked with epibromohydrin or epichlorohydrin. More preferably, the epibromohydrin or epichlorohydrin is present in an amount in the range of between about one and twenty five percent by weight of the cross-linked biodegradable biocompatible polyacetals.

Alternatively, the term "reactive" group as it relates to X$^1$ and X$^2$ means a nucleophilic group that can be reacted with an aldehyde intermediate of the biodegradable biocompatible polyacetals, thereby cross-linking the biodegradable biocompatible polyacetals. Suitable reactive groups for the aldehyde intermediate include amines, thiols, polyols, alcohols, ketones, aldehydes, diazocompounds, boron derivatives, ylides, isonitriles, hydrazines and their derivatives and hydroxylamines and their derivatives, etc.

In one embodiment, the biodegradable biocompatible polyacetals of the present invention have a molecular weight of between about 0.5 and 500 kDa. In a preferred embodiment of the present invention, the biodegradable biocompatible polyacetals have a molecular weight of between about 1 and 300 kDa; 2 and 250 kDa or 20 and 100 kDa.

The biodegradable biocompatible polyacetal of the present invention can be formed by combining a suitable polysaccharide with a molar excess of a glycol-specific oxidizing agent to form an aldehyde intermediate. A "molar excess of a glycol-specific oxidizing agent," as that phrase is employed herein, means an amount of the glycol-specific oxidizing agent that provides oxidative opening of essentially all carbohydrate rings of the polysaccharide. The aldehyde intermediate may then combined with a reducing agent to form the biodegradable biocompatible polyacetal. The biodegradable biocompatible polyacetals of the present invention can form linear or branched structures. The biodegradable biocompatible polyacetal of the present invention can be optically active. Optionally, the biodegradable biocompatible polyacetal of the present invention can be racemic.

Structure, yield and molecular weight of the resultant polyaldehyde depend on the initial polysaccharide. Polysaccharides that do not undergo significant depolymerization in the presence of glycol-specific oxidizing agents, for example, poly (1→6) hexoses, are preferable. Examples of suitable polysaccharides include starch, cellulose, dextran, etc. A particularly preferred polysaccharide is dextran. Examples of suitable glycol-specific oxidizing agents include sodium periodate, lead tetra-acetate, etc. Examples of suitable reducing agents include sodium borohydride, sodium cyanoborohydride, etc.

In an embodiment wherein dextran is employed as a reactant to form the biodegradable biocompatible polyacetal, the glycol-specific oxidation can be conducted at a temperature between about 25° C. and 40° C. for a period of about eight hours at a suitable pH. Temperature, pH and reaction duration can affect the reaction rate and polymer hydrolysis rate. The reaction is preferably conducted in the absence of light. One skilled in the art can optimize the reaction conditions to obtain polymers of desired composition. The resultant aldehyde intermediate can be isolated and combined with a solution of a reducing agent for a period of about two hours to form the biodegradable biocompatible polyacetal after isolation. Alternatively, aldehyde groups can be conjugated with a variety of compounds or converted to other types of functional groups.

It is believed that the carbohydrate rings of a suitable polysaccharide can be oxidized by glycol-specific reagents with cleavage of carbon bonds between carbon atoms that are connected to hydroxyl groups. The following mechanism is an example of what is believed to occur:

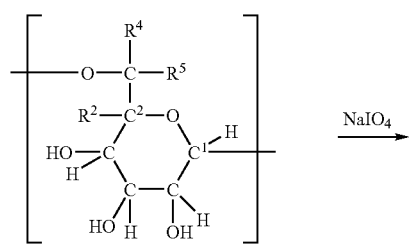

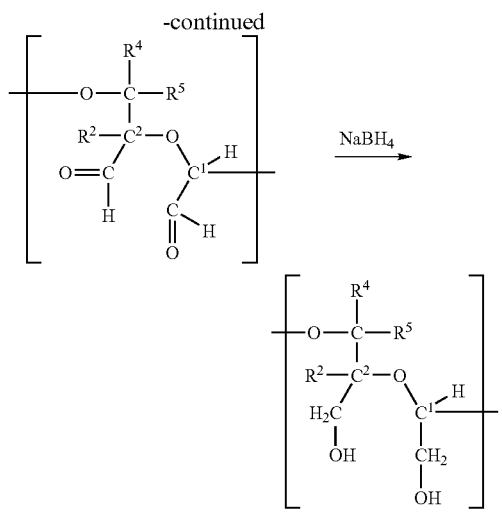

This process can be complicated by the formation of intra and interpolymer hemiacetals which can inhibit further polysaccharide oxidation. However, oxidative opening of the polysaccharide rings can be controlled by controlling the reaction conditions. In the present invention, it can be demonstrated that the polysaccharide oxidation, followed by reduction, causes synthesis of macromolecular biodegradable biocompatible polyacetals. The structure of the biodegradable biocompatible polyacetal obtained by the above mentioned method is dependent upon the precursor polysaccharide. Although it is generally not desirable, the polyacetal can contain intermittent irregularities throughout the polyacetal, such as incompletely oxidized additional groups or moieties in the main chain or in the side chains, as shown below:

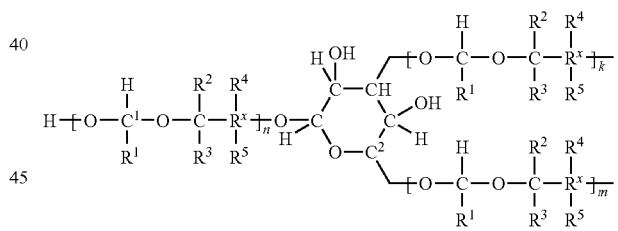

wherein k, m, and n are integers greater than or equal to one.

Since it is believed that oxidation does not affect configurations at the $C^1$ and $C^2$ positions, the aldehyde intermediate and the polyacetal retain the configuration of the parent polysaccharide and are formed in stereoregular isotactic forms.

The resultant biodegradable biocompatible polyacetal can be chemically modified by, for example, cross-linking the polyacetals to form a gel. The cross-link density of the biodegradable biocompatible polyacetal is generally determined by the number of reactive groups in the polyacetal and by the number of cross-linking molecules, and can be controlled by varying the ratio of polyacetal to the amount of cross-linker present.

For example, the biodegradable biocompatible polyacetal can be combined with a suitable aqueous base, such as sodium hydroxide, and cross-linked with epibromohydrin. Control of the amounts of epibromohydrin can determine the degree of cross-linking within the biodegradable biocompatible polyacetal gel. For example, biodegradable biocompatible polyacetals can be exposed to varying amounts of epibromohydrin for a period of about eight hours at a temperature about 80° C. to form cross-linked biodegradable biocompatible polyacetal gels which vary in cross-link density in relation to the amount of epibromohydrin utilized.

Treatment of the biodegradable biocompatible polyacetal with a suitable base, such as triethylamine in dimethylsulfoxide (DMSO), and an anhydride provides, for example, a derivatized polyacetal solution. Control of the amount of anhydride within the biodegradable biocompatible polyacetal can determine the degree of derivitization of the polyacetal in the solution.

Polyacetals of this invention can have a variety of functional groups. For example, aldehyde groups of an intermediate product of polysaccharide oxidation can be converted not only into alcohol groups, but also into amines, thioacetals, carboxylic acids, amides, esters, thioesters, etc.

Terminal groups of the polymers of this invention can differ from $R^1$, $R^2$, $R^3$, $R^4$, and $R^5$. Terminal groups can be created, for example, by selective modification of each reducing and non-reducing terminal unit of the precursor polysaccharide.

One skilled in the art can utilize known chemical reactions to obtain desired products with varying terminal groups. For example, a hemiacetal group at the reduced end of the polyacetal can be readily and selectively transformed into a carboxylic acid group and further into a variety of other functional groups. A primary alcohol group at the non-reduced end can be selectively transformed into an aldehyde group and further into a variety of functional groups.

Alternatively, the biodegradable biocompatible polyacetals of the present invention can be formed by combining a cationic initiator with a precursor compound having the chemical structure:

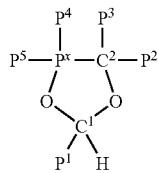

which forms a polymer having the chemical structure:

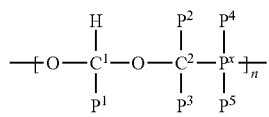

$P^1$ is a protected hydrophilic group which includes a carbon atom covalently attached to $C^1$. $P^x$ includes a carbon atom covalently attached to $C^2$. "n" is an integer. At least one of $P^1$, $P^2$, $P^3$, $P^4$ and $P^5$ is selected from hydrogen and protected hydrophilic groups suitable for conversion. $P^1$, $P^2$, $P^3$, $P^4$ and $P^5$ do not interfere with the cationic polymerization. Furthermore, $P^1$, $P^2$, $P^3$, $P^4$, and $P^5$ are suitable for conversion to hydrophilic groups as described above.

"Protected hydrophilic group," as that term is used herein, means a chemical group which will not interfere with decyclization of the precursor compound by the cationic initiator or subsequent polymerization, and which, upon additional treatment by a suitable agent, can be converted to a hydrophilic functional group. Examples of protected hydrophilic groups include esters, ethers, thioesters, thioethers, vinyl groups, haloalkyl groups, etc.

Other polymers that can be used in the present invention are all biodegradable polymers. These polymers include, but are not limited to, polycarbonates, polyanhydrides, polyorthoesters, polyglycolide (PGA), copolymers of glycolide, poly (glycolide-co-caprolactone) (PGA/PCL), glycolide/L-lactide copolymers (PGA/PLLA), lactide/trimethylene carbonate copolymers (PLA/TMC), glycolide/trimethylene carbonate copolymers (PGA/TMC), polylactides (PLA), stereo-copolymers of PLA, poly-L-lactide (PLLA), poly-DL-lactide (PDLLA), L-lactide/DL-lactide copolymers, copolymers of PLA, lactide/tetramethylglycolide copolymers, lactide/α-valerolactone copolymers, lactide/ε-caprolactone copolymers, hyaluronic acid and its derivatives, polydepsipeptides, PLA/polyethylene oxide copolymers, unsymmetrical 3,6-substituted poly-1,4-dioxane-2,5-diones, carboxymethyl cellulose (CMC), poly-β-hydroxybutyrate (PHBA), PHBA/bhydroxyvalerate copolymers (PHBA/HVA), poly-p-dioxanone (PDS), poly-a-valerlactone, poly-ε-caprolactone, methacrylate-N-vinyl-pyrrolidone copolymers, polyesteramides, polyesters of oxalic acid, polydihydropyranes, polyalkyl-2-cyanoacrylates, polyurethanes, polypeptides, poly-β-malic acid (PMLA), poly-β-alcanoic acids, polybutylene oxalate, polyethylene adipate, polyethylene carbonate, polybutylene carbonate, and other polyesters containing silyl ethers, acetals, or ketals, alginates, and blends or other combinations of the aforementioned polymers. In addition to the aforementioned aliphatic link polymers, other aliphatic polyesters may also be appropriate for producing aromatic/aliphatic polyester copolymers. These include aliphatic polyesters selected from the group of oxalates, malonates, succinates, glutarates, adipates, pimelates, suberates, azelates, sebacates, nonanedioates, glycolates, and mixtures thereof. All of the above polymers are degraded in the body by hydrolysis. The different polymers vary in their structural and chemical aspects, which afford them differences in strength, action, degradation time, and utility.

The biodegradable polymers of the present invention preferably include one or more chemical functional groups through which the biologically active agents can be linked. Those biodegradable polymers which do not contain chemical functional groups may have to be modified in order to introduce chemical functionality into the polymer. For example, the biodegradable polymers poly(lactic acid) and poly(glycolic acid) do not contain any chemically functional groups along the hydrocarbon backbone of the materials to which a biologically active species can be covalently coupled. One strategy that has been proposed for introducing functional groups into poly(lactic acid) is the copolymerization of lactide with a cyclic monomer of lactic acid and the amino acid lysine to create poly(lactic acid-co-lysine) (see U.S. Pat. No. 5,399,665, issued to Barrera, et al.). This copolymer provides side chains that terminate in amino ($NH_2$) groups. These amino groups can be used as attachment sites for the immobilization of bioactive species. Since this method chemically alters the polymer, many of the properties of the polymer are subject to change. For example, the degradation rate and the tensile strength may be effected by the alteration to the polymer.

Certain biodegradable polymers of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, atactic, syndiotactic, isotactic, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular stereoisomeric form of a biodegradable polymer of the present invention is desired, it may be prepared by asymmetric synthesis. Contemplated equivalents of the biodegradable polymeric systems described above include polymers which otherwise correspond thereto, and which have the same general properties thereof, wherein one or more simple variations of substituents are made which do not adversely affect the efficacy of the polymer in treating such disorders as mediated by plaque build up.

The biodegradable polymers may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the biodegradable polymers of the invention, or by separately reacting a purified polymer of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

Pharmaceutically acceptable salts of the subject polymers include the conventional nontoxic salts or quaternary ammonium salts of the compounds, e.g., from non-toxic organic or inorganic acids. For example, such conventional nontoxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

Biodegradable polymers of the present invention may contain one or more acidic functional groups and, thus, are capable of forming pharmaceutically-acceptable salts with pharmaceutically-acceptable bases. These salts can be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

In general, the biodegradable polymers of the present invention may be prepared by the methods illustrated in the Examples, or by modifications thereof, using readily available starting materials, reagents and conventional synthesis procedures. In these reactions, it is also possible to make use of variants which are in themselves known, but are not mentioned here.

Biodegradability of polymers can be determined by assays known in the art, e.g., by the incubation of the polymer in blood or by injection of the polymer into an animal. Biocompatibility of a polymer can also be determined according to methods known in the art.

Exemplary Biologically Active Agents

In one embodiment, the biological agent provided by the invention is a membraneous or soluble polypeptide or protein, e.g., a polypeptide or protein linked to the cellular membrane and having an extracellular domain or a polypeptide or protein secreted from a cell. In a preferred embodiment, the soluble or membrane-bound polypeptide or protein is an enzyme, in particular, an extracellular enzyme, also referred to as an "ectoenzyme."

A preferred ectoenzyme is an ectonucleotidase, i.e., an extracellular nucleotidase. An exemplary ectonucleotidase is a nucleoside triphosphate diphosphohydrolase (NTPDase), also referred to as an "apyrase," "ecto-ATPase," "ecto-ADPase," "nucleotide phosphohydrolase," and "ATP pyrophosphohydrolase" (EC 3.6.1.5). NTPDases are $Ca^{2+}/Mg^{2+}$ dependent ectoenzymes that sequentially hydrolyze nucleoside 5'-triphosphates (NTPs) and nucleoside 5' diphosphates (NDPs). Thus, NTPDases catalyze the sequential phosphorolysis (i.e., removal of phosphate groups) of ATP to ADP to AMP. In general, proteins of this class exhibit non-specificity toward nucleoside di- or triphosphates and towards different nucleoside di- and tri-phosphates. For example, the same enzyme can catalyze the conversion of ATP into ADP and ADP into AMP. The same enzyme may also hydrolyze CTP, CDP, GTP, GDP, TTP, TDP, UTP and/or UDP. These enzymes belong to the E-type ATPase or ecto-ATPase family, of which the members degrade nucleotide tri-and/or diphosphates, but not monophosphates (Plesner L. (1995) Int. Rev. Cytol. 158:141).

An exemplary NTPDase that can be used according to the invention is NTPDase-1, also referred to as "CD39," which is a 78 kDa glycosylated protein. This protein was originally described as a B-cell activation marker. Human CD39 is a protein of 510 amino acids, encoded by a cDNA of 1704 nucleotides. The nucleotide and amino acid sequences of human CD39 can be found under GenBank Accession No. U87967 and S73813; in Kaczmarek et al. (1996) J. Biol. Chem. 271: 33116; Maliszewski et al. (1994) J. Immunol. 153:3574; WO 96/30532 and in WO 00/23459. The nucleotide sequence is set forth as SEQ DI NO: 1 and the encoded amino acid sequence (encoded by nucleotides 31 to 1563) is set forth as SEQ ID NO: 2 and shown in FIG. 1.

CD39 contains two putative transmembrane regions located near the N- and C-termini, respectively. These regions are likely to be used for anchoring of the protein to the cell membrane. The portion of the molecule that is between these two putative transmembrane regions forms a loop that is external to the cell and contains five small Apyrase-Conserved Regions (ACRs; ACR1 to ACR5; see, Schulte et al. (1999) Biochemistry 38:2248 and FIG. 1). ACR1 corresponds to amino acids 54-61 of SEQ ID NO: 2; ACR2 corresponds to amino acids 125-135 of SEQ ID NO: 2; ACR3 corresponds to amino acids 171-183 of SEQ ID NO: 2; ACR4 corresponds to amino acids 213 to 220 of SEQ ID NO: 2 and ACR5 corresponds to amino acids 447-454 of SEQ ID NO: 2 (Kaczmarek et al. (1996), J. Biol. Chem. 271:33116 and Schulte et al., supra). These ACRs are characteristic of apyrases and are involved in the enzymatic activity of apyrases.

In particular, intact ACR1, ACR4 and ACR5 within CD39 are involved in biochemical activity (Schulte et al., supra). Removal of the N- or C-terminal transmembrane regions did not dramatically affect biological activity when the enzyme was coupled to a GPI-anchor (Schulte et al., supra). A putative ATP-binding domain is located at amino acids 52-58 of SEQ ID NO: 2.

CD39 also has six potential N-linked glycosylation sites and 11 cysteine residues that may be implicated in the formation of oligomers. Glycosylation does not appear to affect activity of the enzyme, but this remains to be evaluated (Schulte et al., supra). There are also several sites that may be modified by ectoprotein kinases and potential intracellular protein kinase C phosphorylation sites (Schulte et al., supra). CD39 also undergoes plamitoylation within the N-terminal intracytoplasmic region on the cysteine at amino acid 13 (Koziak et al. (2000) J. Biol. Chem. 275:2057). CD39 undergoes multimerization (Schulte et al., supra).

Another exemplary apyrase is CD39L1 (or NTPDase-2). Other apyrases that can be used include CD39L2 (or NTPDase-6); CD39L3; and CD39L4 (or NTPDase-5) (see, e.g., Chadwick and Frischauff(1998) Genome 50:357). The nucleotide sequence of CD39-L4 is set forth in Chadwick and Frischauff(1998) Genome 50:357. Similarly to CD39, CD39-L1 and CD39-L3 have hydrophobic domains at their N- and C-termini. CD39-L2 and CD39-L4, however, have a hydrophobic region only at their N-terminus and are potentially soluble ecto-enzymes postcleavage.

Whereas CD39 (NTPDase1) hydrolyzes ATPs and ADPs at about the same rate, CD39-L1 (NTPDase2) hydrolyzes preferentially ATP over ADP. In particular, whereas recombinant NTPDase 1 hydrolyzes ATP to AMP with the formation of only minor amounts of free ADP, ADP appears as the major free product when ATP is hydrolyzed by NTPDase2 (Heine et al. (2001) Eur J Biochem 268:364. Experiments with chimeric enzymes comprising portions of each of the NTPDases showed that amino-acid residues between ACR3 and ACR5 and in particular the cysteine-rich region between ACR4 and ACR5 conferred a phenotype to the chimeric enzymes that corresponded to the respective wild-type enzyme. These results indicated that protein structure rather than the conserved ACRs may be of major relevance for determining differences in the catalytic properties between the related wild-type enzymes (Heine et al., supra).

CD39-L4 hydrolyzes NDP preferably over NTP. For example, it has been described that CD39-L4 hydrolyze ADP at a rate of about 20 fold higher than that of ATP (Mulero et al. (1999) J. Biol. Chem. 274:20064).

In some embodiments, the apyrase is a non-mammalian or non-animal apyrase, e.g., apyrase from potato (Handa and Guidotti (1996) Biochem. Biophys. Res. Comm. 218:916 and GenBank Accession number U58597). The nucleotide and amino acid sequences of potato apyrase are set forth as SEQ ID NOs: 3 and 4, respectively.

GenBank Accession numbers for nucleic acids encoding exemplary apyrases are set forth below:
U87967: Human ATP diphosphohydrolase;
S73813: CD39=lymphoid cell activation antigen [human, B lymhpoblastoid cell line, MP-1];
XM 055699, XM 055698, XM 005712 and XM 051047: Homo sapiens ectonucleoside triphosphate diphosphohydrolase 1;
NM 020354 and AF269255: Homo sapiens lysosomal apyrase-like protein 1 (LALP1);
AF 034840: Homo sapiens E-type ATPase (HB6);
NM 001249: Homo sapiens ectonucleoside triphosphate diphosphohydrolase 5 (ENTPD5):
NM 001248: Homo sapiens ectonucleoside triphosphate diphosphohydrolase 3 (ENTPD3):
NM 001247: Homo sapiens ectonucleoside triphosphate diphosphohydrolase 6 (putative function) (ENTPD6);
NM 001246: Homo sapiens ectonucleoside triphosphate diphosphohydrolase 2 (ENTPD2);
NM 001776: Homo sapiens ectonucleoside triphosphate diphosphohydrolase 1 (ENTPD1);
NM 053103: Mus musculus lysosomal apyrase-like 2 (Lysal2);
AV254553 RIKEN full-length enriched, adult male testis (DH10B) Mus musculus cDNA;
AF 288221: Mus musculus LALP1;
NM 009849: Mus musculus ectonucleoside triphosphate diphosphohydrolase 2 (Entpd2);
NM 009848: Mus musculus ectonucleoside triphosphate diphosphohydrolase 1 (Entpd1);
NM 007647: Mus musculus ectonucleoside triphosphate diphosphohydrolase 5 (Entpd5);
NM 022587: Rattus norvegicus ecto-apyrase (U81295);
AF 041048: Drosophila melanogaster CD39-like NTPase gene;
AF 005940: Bos taurus ecto-apyrase CD39;
U58597 and P80595: Solanum tuberosum (potato) ATP-diphosphohydrolase (RROP1);
P32621 Saccharomyces cerevisiae DGA1 guanosine diphosphatase;
S48859: pea NTP-ase, P. sativum (garden pea) nucleoside triphosphatase; and
gi1049394:C. elegans cosmid.

Yet other apyrases, such as Shistosoma mansoni, are described in Vasconcelos et al. (1996) J. Biol. Chem. 271: 22139.

Other apyrase and apyrase-type genes that can be used according to the invention can be found in GenBank.

The amino acid sequences of potato apyrase and that of other NTPDases have a high degree of similarity, particularly within several small Apyrase-Conserved Regions (ACRs).

Another sequence that is conserved among apyrases is (I/V)(V/M/I)(I/L/F/C)DAGS(S/T) (SEQ ID NO: 5), which is located near the amio-terminal of the apyrases (see Vasconcelos et al., supra). Sequences of strong homology between potato apyrase and pea NTPase include PGLSSYA (SEQ ID NO: 6) and LYVHSYL (SEQ ID NO: 7) (see Vasconcelos et al., supra).

Fragments of apyrases can also be used according to the invention. Preferred fragments retain at least some of the biological activity of the full-length apyrase. Exemplary fragments consists of at least about 50, 100, 200, 300, or 500 amino acids. In one embodiment, an apyrase lacking one or both of the hydrophobic regions is used, such that the apyrase is soluble and not membrane bound. Accordingly, for example, a polypeptide having about amino acids 37 to about 510 of SEQ ID NO: 2 (lacking the N-terminal transmembrane region); amino acids 1 to about 477 of SEQ ID NO: 2 (lacking the C-terminal transmembrane region); about amino acids 37 to about 477 of SEQ ID NO: 2 (lacking both N- and C-terminal transmembrane region) can be used (Schulte et al., supra). Fragments of apyrases may contain only the portion that is external to the cell and contains one or more of the ACRs. Preferred fragments include ACR-1, ACR4 and/or ACR5. NTPDase proteins lacking ACR-2 and/or ACR3 can be used according to the invention. Mutants wherein one of the transmembrane regions or ACRs is mutated, rather than deleted can also be used according to the invention. The biological activity of fragments can be tested as further described herein.

Preferred apyrases (or apyrases conjugated to a polymer) of the invention have a greater affinity for ADP than for ATP. For example, preferred apyrases or fragments of homologs may have an affinity constant (Kd) for ADP of at least about $10^{-6}$ M, $10^{-7}$ M, $10^{-8}$ M, or $10^{-9}$ M, and an affinity constant for ATP of at most about $10^{-6}$ M or $10^{-7}$ M. Apyrases may have an affinity for ADP that is at least 2 fold, 5 fold, 10 fold, 20 fold, 50 fold or 100 fold higher than that for ATP. In other embodiments, an apyrase will have a greater affinity for ATP than for ADP.

Apyrases may have an ADPase or ATPase activity of at least about 50, preferably at least about 100, 500, 1,000, 2,000, 3,000, 5,000, or 10,000 nmol Pi $min^{-1}$ $mg^{-1}$ as measured in an ADPase assay, e.g., as described herein.

Another ectonucleotidase is ecto-5'nucleotidase (CD73; EC 3.1.3.5), which catalyzes the hydrolysis of nucleoside 5'-monophosphates, such as AMP, UMP and GMP, and generates the respective nucleosides that may be taken up by specific membrane transporters (Zimmerman H. (1992) Biochem. J. 285:345). Other ectonucleosidases that can be used according to the invention include members of the family of ecto-phosphdiesterase/nucleotide pyrophosphatase or PDNP family (Goding et al. (1998) Immunol. Rev. 161:11). One member of the PDNP family is is the glycoprotein PC-1, which has two enzymatic activities, i.e., a 5' nucleotide phosphodiesterase activity (EC 3.1.4.1) and a nucleotide pyrophosphatase activity (EC 3.6.1.9), and is capable of hydrolyzing 3', 5'-cAMP to AMP, or ATP to AMP and pyrophosphate (Belli and Goding (1994) Eur. J. Biochem. 226:443). Another ectoenzyme involved in regulating local extracellular concentrations of nucleosides is adenosine deaminase (ADA; EC 3.5.4.4), which degrades adenosine to inosine.

In other embodiments, the biological agent is a secreted polypeptide or protein which is not necessarily an enzyme. For example, the biological agent can be an interleukin, a lymphokine, a hormone, a growth factor, a differentiation factor, a complement factor, or a soluble form of a membrane protein, e.g., a cell surface receptor. The biological agent can be, e.g., an interferon, such as interferon-α, -β, or -γ. Portions of secreted polypeptides or proteins can also be used.

Biological agents that can be used include polypeptides encoded by any form of a gene, i.e., by any allele of the gene or mutated versions of the gene, provided that the desired biological activity is present.

The biological agents can originate from any species, including plants and animals. In some embodiments, the biological agent is from a mammal, e.g., a human, a non-human primate, an ovine, a bovine, a porcine, an equine, a feline, a canine or an avian. Nucleotide and amino acid sequences of such homologs may be known in the art or can be determined by isolating the corresponding homolog and determining the nucleotide sequence. Isolating orthologs or a gene can be performed by hybridization under non stringent conditions as further described herein, or by PCT using degenerate primers. Such methods are known in the art. Considering that apyrases are present in distant evolutionary species, isolation of additional apyrases, is within the skill in the art.

Other biological agents that can be used include homologs of wild-type polypeptide, e.g., apyrases, e.g., those described above. "Homologs" of apyrases refers to polypeptides having a significant degree of homology (identity or similarity) in amino acid sequence and biological activity to wild-type apyrases. Homologs include polypeptides differing from wild-type polypeptides in one or more amino acid substitution, deletion or addition. For example, an homolog of a wild-type apyrase can have from 1 to 50 amino acid substitutions, deletions or additions, preferably from 1 to 25, even more preferably from 1 to 15, from 1 to 10 or from 1 to 5 amino acid substitutions, deletions or additions.

Accordingly, the biological agent can be a polypeptide which is a least about 70%, at least about 80%, at least about 90%, at least about 95%, at least about 97% or at least about 99% identical or homologous to that of the wild-type counterpart polypeptide or portion thereof, provided that the polypeptide has the desired biological activity. Based on the description of wild-type polypeptides provided herein and further described in publications, a person of skill in the art would know where amino acid substitutions can be made without significantly affecting the biological activity of the polypeptide. The biological activity of such homologues can also be tested as further described herein, or according to methods known in the art.

Homologs of naturally occurring polypeptides within the scope of the invention are those that are encoded by nucleic acids which hybridize under stringent conditions to nucleic acids of wild-type polypeptides, e.g., the nucleic acid encoding human CD39, e.g., set forth as SEQ ID Nos: 1. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature of salt concentration may be held constant while the other variable is changed. In a preferred embodiment, a nucleic acid encoding a mutated PDGFR of the present invention will hybridize to SEQ ID NOs: 1 or GenBank Accession numbers set forth herein or complement thereof under moderately stringent conditions, for example at about 2.0×SSC and about 40° C.

Other homologs, e.g., homologs of an apyrase, include those which differ from the wild-type polypeptide by conservative amino acid substitutions. Preferred homologs contain from 1 to 20, amino acid substitutions, preferably from 1 to 10 and even more preferably from 1 to 5 amino acid substitutions. It is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2.sup.nd ed., Ed. by L. Stryer, WH Freeman and Co.: 1981).

In yet other embodiments, a biological agent is fused to a heterologous polypeptide. For example, a polypeptide may be fused in frame to a marker sequence, also referred to herein as "Tag sequence" encoding a "Tag peptide", which allows for marking and/or purification of the polypeptide of the present invention. In a preferred embodiment, the marker sequence is a hexahistidine tag, e.g., supplied by a PQE-9 vector. Numerous other Tag peptides are available commercially. Other frequently used Tags include myc-epitopes (e.g., see Ellison et al. (1991) *J Biol Chem* 266:21150-21157), which includes a 10-residue sequence from c-myc, the pFLAG system (International Biotechnologies, Inc.), the pEZZ-protein A system (Pharmacia, N.J.), and a 16 amino acid portion of the Haemophilus influenza hemagglutinin protein. Polypeptides may also be fused to a maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and InVitrogen, respectively. Furthermore, any polypeptide can be used as a Tag so long as a reagent, e.g., an antibody interacting specifically with the Tag polypeptide is available or can be prepared or identified.

In another embodiment, a fusion polypeptide, e.g., a polypeptide having a poly-(His) Tag further comprises a cleavage site located between the polypeptide and the Tag, thereby allowing the Tag to be removed following the purification step using the Tag. For example, the cleavage site can be a consensus sequence that is recognized by proteases. The site can be, e.g., an enterokinase cleavage site which is cleavable with enterokinase (e.g., see Hochuli et al. (1987) J. Chromatography 411:177; and Janknecht et al. PNAS 88:8972).

Alternatively, a heterologous polypeptide may be added for stabilizing the protein; or for facilitating the folding of the polypeptide or for prolonging its half-life. For example, a polypeptide may be fused to an immunoglobulin constant region (see, e.g., U.S. Pat. No. 5,434,131).

Polypeptides may also be chemically modified to create derivatives by forming covalent or aggregate conjugates with other chemical moieties, such as glycosyl groups, lipids, phosphate, acetyl groups and the like. Covalent derivatives of proteins can be prepared by linking the chemical moieties to functional groups on amino acid sidechains of the protein or at the N-terminus or at the C-terminus of the polypeptide.

Biologically active agents may also be labeled, which help in the detection of the conjugate. A label can be radioactive or non-radioactive. When the conjugate is administered to a subject, any label suitable for administration to a subject can be used. Numerous labels and methods for attaching them to molecules are known in the art.

In another embodiment, an enzyme may be subjected to limited proteolysis prior to linking to a polymer. For example, apyrase can be incubated at 37° C. with about 3.3 μg/ml trypsin (Life Technologies, Grand Island, N.Y.) for about 5 minutes or in 0.3% Triton X-100 with 0.25 units of N-glycosidase F (Life Technologies, Grand Island, N.Y.) for 12 hours. The reaction can be stopped with PMSF at a final concentration of about 1 mM. This is further described in Schulte et al., supra.

Methods of Making Biological Agents

Biological agents can be prepared according to methods known in the art. For example, polypeptides or proteins can be isolated from their natural environment; they can be synthesized de novo, or they can be produced by recombinant technology.

In a preferred embodiment, a polypeptide is produced recombinantly. In an illustrative embodiment, a nucleic acid encoding the polypeptide and operably linked to at least one transcriptional regulatory sequence, such as a promoter, is introduced into a host cell, the polypeptide is expressed in the cell or is secreted from the cell, and the polypeptide is isolated. The host cell can be a eukaryotic (e.g., yeast, avian, insect, mammalian or plant) or a prokaryotic cell (e.g., bacterial). Alternatively, the polypeptide can be synthesized in lysates. For example, RNA can be synthesized in vitro, and the RNA can be translated into polypeptide in a reticulocyte lysate or wheat germ extract, according to methods known in the art.

Preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and phyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2.sup.nd Ed., ed. by Sambrook, Fritsch and Maniatis (Cold Spring Harbor Laboratory Press: 1989) Chapters 16 and 17.

A number of types of cells may act as suitable host cells for expression of a protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Suitable vectors for the expression of a polypeptide in prokaryotes, e.g., *E. coli,* include plasmids of the types: pBR322-derived plasmids, pEMBL-derived plasmids, pEX-derived plasmids, pBTac-derived plasmids and pUC-derived plasmids. Potentially suitable bacterial strains include *Escherichia coli, Bacillus subtilis, Salmonella typhimurium,* or any bacterial strain capable of expressing heterologous proteins.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in *S. cerevisiae* due to the replication determinant of the yeast 2 micron plasmid. In addition, drug resistance markers such as ampicillin can be used. Potentially suitable yeast strains include *Saccharomyces cerevisiae,*

Schizosaccharomyces pombe, Kluyveromyces strains, Candida, or any yeast strain capable of expressing heterologous proteins.

In some instances, it may be desirable to express the recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the .beta.-gal containing pBlueBac III).

When it is desirable to express only a portion of a protein, such as a form lacking a portion of the N- or C-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) J. Bacteriol. 169:751-757) and Salmonella typhimurium and its in vitro activity has been demonstrated on recombinant proteins (Miller et al. (1987) PNAS 84:2718-1722). Therefore, removal of an N-terminal methionine, if desired, can be achieved either in vivo by expressing the derived polypeptides in a host which produces MAP (e.g., E. coli or CM89 or S. cerevisiae), or in vitro by use of purified MAP (e.g., procedure of Miller et al., supra).

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl™ or Cibacrom blue 3GA Sepharose™; one or more steps involving hydrophobic interaction chromatography using such resins as phenyl ether, butyl ether, or propyl ether; or immunoaffinity chromatography.

One or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. Purification of proteins is further described, e.g., in Robert K Scopes "Protein Purification: Principles and Practice" Third Ed. Springer-Verlag, N.Y. 1994. The protein thus purified is substantially free of other mammalian proteins and is defined in accordance with the present invention as an "isolated protein."

For example, soluble human CD39 or portions thereof can be prepared, e.g., by expression of a construct expressing the CD39 or portions thereof in a host cell, e.g., COS-1 and CHO cells, as described, e.g., in Gayle et al. (1998) J. Clin. Invest. 101:1851 and in Kacmarek et al. (1996), supra. Preferred portions are fragments that do not include one or both of the transmembrane domains. The CD39 or portion thereof can then be isolated from the supernatant of the culture by methods including, e.g., affinity chromatrography using an antibody binding specifically to the CD39 or portion thereof.

The polypeptides can also be produced in an in vitro system, e.g., in an in vitro transcription and translation system. Many vectors for in vitro transcription are available commercially. These may contain one or more of the promoters SP6, T3 and T7 and may additionally contain a polyA sequence at the 3' end of the polylinker in which the DNA of interest is inserted. A "polylinker" refers to a nucleotide sequence containing several restriction enzyme recognition sites. Examples of vectors include the series of SP6 vectors, e.g.,. SP64 (Krieg and Melton, infra), BlueScript, and pCS2+. Vectors that can be used for in vitro transcription are also described, e.g., in U.S. Pat. No. 4,766,072. In vitro transcription can be conducted with a nucleic acid that is not per se a vector, but merely contains the elements necessary for in vitro transcription. For example, such a template nucleic acid may comprise an RNA polymerase promoter located upstream of the sequence to transcribe. Such template nucleic acid can be obtained, e.g., by polymerase chain reaction (PCR) amplification of a sequence of interest using a primer that contains an RNA polymerase promoter. PCR amplification methods are well known in the art.

An in vitro transcription reaction can be carried out according to methods well known in the art. Kits for performing in vitro transcription kits are also commercially available from several manufacturers. In an illustrative embodiment, an in vitro transcription reaction is carried out as follows. A vector containing an RNA Polymerase promoter and an insert of interest is preferably first linearized downstream of the insert, by e.g., restriction digest with an appropriate restriction enzyme. The linearized DNA is then incubated for about 1 hour at 37 or 40° C. (depending on the RNA polymerase) in the presence of ribonucleotides, an RNAase inhibitor, an RNA polymerase recognizing the promoter that is operably linked upstream of the insert to be transcribed, and an appropriate buffer containing Tris.Cl, $MgCl_2$, spermidine and NaCl. Following the transcription reaction, RNAase free DNAse can be added to remove the DNA template and the RNA can be purified by, e.g., a phenol-chlorophorm extraction. Usually about 5-10 μg of RNA can be obtained per microgram of template DNA. Further details regarding this protocol are set forth, e.g., in Molecular Cloning A Laboratory Manual, 2nd Ed., ed. by Sambrook, Fritsch and Maniatis (Cold Spring Harbor Laboratory Press: 1989).

In another embodiment, the RNA is "capped" prior to contacting it with an in vitro translation system. In certain situations, efficient translation of eukaryotic RNA requires that the 5' end of an RNA molecule is "capped", i.e., that the 5' nucleotide at the 5' end of the RNA has a 5'-5' linkage with a 7-methylguanylate ("7-methyl G") residue. The presence of a 7-methyl G on an RNA molecule in a 5'-5' linkage is referred to as a "cap." It has been proposed that recognition of the translational start site in mRNA by the eukaryotic ribosomes involves recognition of the cap, followed by binding to specific sequences surrounding the initiation codon on the RNA. Accordingly, it is possible that in certain embodiments of the invention, capping of the RNA synthesized in vitro prior to contacting the RNA with an in vitro translation system improves the translation efficiency of the RNA. Thus, in one embodiment, the RNA is contacted with methyl-7 (5')PPP(5') guanylate (available, e.g., from Boehringer Mannheim Biochemicals) in the presence of an in vitro transcription reaction mixture, to obtain capped RNA. In the case of in vitro transcribed RNA, capping is preferably carried out during in vitro transcription, but can also be carried out during in vitro translation by, e.g., addition of a cap analog (GpppG or a methylated derivative thereof). Cap analogs and protocols pertaining to their use are commercially available, e.g, in in vitro transcription and/or translation kits.

In vitro synthesized RNA can be in vitro translated using an in vitro translation system. The term "in vitro translation system," which is used herein interchangeably with the term "cell-free translation system" refers to a translation system which is a cell-free extract containing at least the minimum elements necessary for translation of an RNA molecule into a protein. An in vitro translation system typically comprises at least ribosomes, $^tRNAS$, initiator methionyl-$^tRNA^{Met}$, proteins or complexes involved in translation, e.g., eIF$_2$, eIF$_3$, the cap-binding (CB) complex, comprising the cap-binding protein (CBP) and eukaryotic initiation factor 4F (eIF$_{4F}$). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes.

In cases where plant expression vectors are used, the expression of a polypeptide of the invention may be driven by any of a number of promoters. For example, viral promoters such as the 35S RNA and 19S RNA promoters of CaMV (Brisson et al., 1984, Nature, 310:511-514), or the coat protein promoter of TMV (Takamatsu et al., 1987, EMBO J., 6:307-311) may be used; alternatively, plant promoters such as the small subunit of RUBISCO (Coruzzi et al., 1994, EMBO J., 3:1671-1680; Broglie et al., 1984, Science, 224: 838-843); or heat shock promoters, eg., soybean hsp 17.5-E or hsp 17.3-B (Gurley et al., 1986, Mol. Cell. Biol., 6:559-565) may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, Methods for Plant Molecular Biology, Academic Press, New York, Section VIII, pp. 421-463; and Grierson & Corey, 1988, Plant Molecular Biology, 2d Ed., Blackie, London, Ch. 7-9.

An alternative expression system which can be used to express a polypeptide of the invention is an insect system. In one such system, *Autographa californica* nuclear polyhedrosis virus (AcNPV) is used as a vector to express foreign genes. The virus grows in *Spodoptera frugiperda* cells. The PGHS-2 sequence may be cloned into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Virol., 46:584, Smith, U.S. Pat. No. 4,215,051).

In a specific embodiment of an insect system, the DNA encoding the subject polypeptide is cloned into the pBlueBacEIII recombinant transfer vector (Invitrogen, San Diego, Calif.) downstream of the polyhedrin promoter and transfected into Sf9 insect cells (derived from *Spodoptera frugiperda* ovarian cells, available from Invitrogen, San Diego, Calif.) to generate recombinant virus. After plaque purification of the recombinant virus high-titer viral stocks are prepared that in turn would be used to infect Sf9 or High Five™ (BTI-TN-5B1-4 cells derived from Trichoplusia ni egg cell homogenates; available from Invitrogen, San Diego, Calif.) insect cells, to produce large quantities of appropriately post-translationally modified subject polypeptide. Although it is possible that these cells themselves could be directly useful for drug assays, the subject polypeptides prepared by this method can be used for in vitro assays.

In another embodiment, the subject polypeptides are expressed in transgenic animals, such that in certain embodiments, the polypeptide is secreted, e.g., in the milk of a female animal.

Alternatively, apyrases can be isolated from tissue. For example, CD39 can be isolated from vascular endothelial cells or placenta, which are known to constitutively express a cell-surface ADPDase or NTPDase. Apyrases can be isolated from plant material (e.g., potato) as described,. e.g., in Handa and Guidotti (1996) Biochem. Biophys. Res. Commun. 218: 916.

Nucleic acids for use in recombinant technology are known in the art, and can be found, e.g., in GenBank. Purification methods for each of these biological agents are described in the art, or they can be derived from purification methods of other, e.g., similar, biological agents.

Homologs and fragments of wild-type polypeptides, e.g., homologs and fragments having one or more amino acid deletions, substitutions or additions, which retain at least a significant amount of the biological activity of the wild-type polypeptide can be obtained by creating combinatorial libraries and screening of these libraries for the desired activity. In one embodiment, the variegated library of variants is generated by combinatorial mutagenesis at the nucleic acid level, and is encoded by a variegated gene library. For instance, a mixture of synthetic oligonucleotides can be enzymatically ligated into gene sequences such that the degenerate set of potential sequences are expressible as individual polypeptides, or alternatively, as a set of larger fusion proteins (e.g., for phage display) containing the set of sequences therein.

There are many ways by which such libraries of potential homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential homolog sequences. The synthesis of degenerate oligonucleotides is well known in the art (see for example, Narang, S A (1983) Tetrahedron 39:3; Itakura et al. (1981) Recombinant DNA, Proc 3.sup.rd Cleveland Sympos. Macromolecules, ed. A G Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386-390; Roberts et al. (1992) PNAS 89:2429-2433; Devlin et al. (1990) Science 249: 404-406; Cwirla et al. (1990) PNAS 87: 6378-6382; as well as U.S. Pat. Nos. 5,223,409, 5,198,346, and 5,096,815).

Likewise, a library of coding sequence fragments can be provided for a clone in order to generate a variegated population of fragments of the gene of interest for screening and subsequent selection of bioactive fragments. A variety of techniques are known in the art for generating such libraries, including chemical synthesis. In one embodiment, a library of coding sequence fragments can be generated by (i) treating a double stranded PCR fragment of a coding sequence of interest with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with SI nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

Combinatorial mutagenesis has a potential to generate very large libraries of mutant proteins, e.g., in the order of $10^{26}$ molecules. Recrusive ensemble mutagenesis (REM) can be used to allow one to avoid the very high proportion of non-functional proteins in a random library and simply enhances the frequency of functional proteins, thus decreasing the complexity required to achieve a usefull sampling of sequence space. REM is an algorithm which enhances the frequency of functional mutants in a library when an appropriate selection or screening method is employed (Arkin and Yourvan, 1992, PNAS USA 89:7811-7815; Yourvan et al., 1992, Parallel Problem Solving from Nature, 2., In Maenner and Manderick, eds., Elsevir Publishing Co., Amsterdam, pp. 401-410; Delgrave et al., 1993, Protein Engineering 6(3):327-331).

The invention also provides for reduction of proteins to generate mimetics, e.g., peptide or non-pepide agents, such as small molecules. Thus, such mutagenic techniques as described above are also useful to map the determinants of the proteins which participate in biological activity. To illustrate, the critical residues of a subject apyrase which are involved in enzymatic activity can be determined and used to generate peptidomimetics or small molecules which have the same biological activity or which act as competitive inhibitors. By employing, for example, scanning mutagenesis to map the amino acid residues of the subject proteins which are involved in biological activity, e.g., enzymatic activity, peptidomimetic compounds can be generated which mimic those residues of the protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffinan et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9.sup.th American Peptide Symposium) Pierce Chemical Co. Rockland, Ill., 1985), b-turn dipeptide cores (Nagai et al. (1985) Tetrahedron Lett 26:647; and Sato et al. (1986) J Chem Soc Perkin Trans 1:1231), and b-aminoalcohols (Gordon et al. (1985) Biochem Biophys Res Communl26:419; and Dann et al. (1986) Biochem Biophys Res Commun 134:71).

Peptides can also be isolated by phage display, as known in the art.

The amount of a protein, e.g., synthesized or purified as described herein, can be determined by the Coomassie protein assay according to the manufacturer's instructions (Bio-Rad). The amount and purity of proteins can also be determined by subjecting the protein mixtures to SDS-PAGE, optionally followed by Western blot analysis. SDS-PAGE gels can be stained, e.g., silver or Coomassie blue stained, for visualizing polypeptides. Western blots can also be incubated with a reagent binding specifically to the subject polylpeptide, e.g., an antibody. The inclusion of known amounts of reference proteins permit, by comparison, to estimate the quantity of a particular protein on the Western blot. Protocols for Western blot analysis are known in the art:

Those skilled in the art will appreciate that the purity of the polypeptide preparation of the invention can be determined by various methods. A preferred method for determining the amount of contaminating proteins in a polypeptide preparation comprises subjecting the polypeptide preparation to gel electrophoresis, e.g., polyacrylamide electrophoresis, in the presence of specific amounts of molecular markers, and staining the gel after the electrophoresis with a protein dye. A comparison of the intensity of the band of the subject polypeptide with the molecular markers indicates the purity of the subject polypeptide preparation. Other methods for determining the amount of contaminating proteins include mass spectrometry, gel filtration and peptide sequencing according to methods known in the art.

A preferred method for determining the amount of contaminating cellular material in a polypeptide preparation comprises gel electrophoresis and silver staining of the gel. Other methods for determining the purity of a polypeptide preparation include mass spectrometry according to methods known in the art. Yet other measurements of the purity of a polypeptide preparation include a measure of the activity of the polypeptide, as further described herein.

Protein concentrations can be determined according to the following methods: Lowry-Folin-Ciocalteau reagent; UV absorption at 280 nm (aromatic band) or 205-220 nm (peptide band); dye binding (e.g., Coomassie Blue G-250); or bis-cinchonic acid (BCA; Pierce Chemicals (Rockford, Ill.)) reagent. All of these methods are described in, e.g., Robert K. Scopes, Protein Purification, Principles and Practice, Third Ed., Springer Verlag New York, 1993, and references cited therein. Briefly, the well-known Lowry method is a relatively sensitive method giving a good color with 0.1 mg/ml or protein or less. The method using Coomassie Blue G-250 is very sensitive, fast and at least as accurate as the Lowry method. The procedure consists in mixing a polypeptide sample with the reagent and measure the blue color at 595 nm.

Those skilled in the art will understand that a preferred method for determining exact protein amounts is by dry weight determination, since it provides a suitably accurate measurement of protein amount. Thus, in a preferred embodiment for determining the amount of the purified polypeptide of the invention, the dry weight of a highly pure preparation of the polypeptide of the invention is determined, and this preparation is then used as a standard for determining the protein concentration of other preparations of polypeptides of the invention.

As those skilled in the art will understand, the percent recovery and degree of purity of a preparation of polypeptide of the invention can be calculated from the total amount of protein recovered after purification and the amount and/or activity of the polypeptide of interest.

Attachment of the Biologically Active Agent to a Biodegradable Polymer

The conjugates of the invention comprise a biologically active agent and a polymer. These two elements can be linked covalently. Alternatively, these two elements can form a non-covalently linked complex, and maintained together, e.g., through ionic interactions or hydrogen bonding.

The attachment of a biologically active material is either done directly to the biodegradable polymeric backbone, or through a pendant chain off of the polymeric backbone. The term "attachment" and its derivatives refer to covalent bonding, hydrogen bonding, or ionic bonding of a bioactive species to a biodegradable polymer.

Ionic attachment may be employed in cases where the biodegradable polymer is either positively or negatively charged and the biologically active agent carries the opposite charge or wherein at least a portion of the biologically active agent carries the opposite charge. The oppositely charged components are held together through electrostatic forces. The charge on the biodegradable polymer may exist naturally, as is the case with the anionic alginate or CMC, or through modification. For example, carbonyl groups can be rendered positively charged through the reaction with secondary amines to form cationic imine complexes. Quarternary nitrogens as in the previous example are commonly used as a source of positive charges in polymers. Any of the previously discussed biodegradable polymers modified with a quartenary nitrogen may be used in ionically attached biologically active agent complexes. Charges on the biologically active compound may originate, for example, from the amino acids of a peptide chain. Deprotonated acid groups or protonated amines are a source of anionic and cationic charges respectively. Attachment is carried out by admixing the two oppositely charged components together in a suitable solvent or more preferably a buffer solution wherein the two species maintain their charges.

For hydrogen atoms bonded to electronegative elements dipole-dipole interaction is uniquely important and forms the basis of hydrogen bonding. Although hydrogen bonds are weak (about 5 kcal mole$^{-1}$ per hydrogen bond) they play an important role in proteins and enzymes where a polypeptide chain contains many C=O and N—H groups. The total amount of bonding that results from many small interactions is substantial and plays an important role in the actual shape or conformation of the protein. Reciprical hydrogen bonding may occur between the C=O and N—H groups of different chains and thus bind them together. In this same fashion, binding may occur with the C=O and N—H groups of the biodegradable polymer. As with the ionic complexes discussed above, preparation of biologically active agents hydrogen bonded to biodegradable polymers can be prepared by admixing the two in a suitable solvent. Due to the weaker bonding interactions of the hydrogen bonds, these complexes may be desirable when increased rates of release of the biologically active agent are wanted.

Preferably, the biologically active agents in the present invention are covalently conjugated to the biodegradable polymer. Biologically active species can be attached to a biodegradable polymer using mild bioconjugation techniques known to those skilled in the art (See K. Mosbach, *Immobilized Enzymes and Cells*, Part B, Academic Press (Orlando, Fla.), (1987); G. T. Hermanson, A. K. Mallia, P. K. Smith, "*Immobilized Affinity Ligand Techniques,*" Academic Press, San Diego, (1992); and S. F. Karel, S. B. Libicki, C. R. Robertson, "*The Immobilization of Whole Cells: Engineering Principles,*" Chemical Eng. Sci., 40: 1321 (1985), for example). Mild bioconjugation schemes are preferred for attachment of bioactive species in order to eliminate or minimize damage to the structure of the biodegradable polymer.

In some circumstances, the interaction of a polymer with the attached bioactive species may be suboptimal. For example, steric hindrances between the biodegradable polymer and the attached bioactive species may limit the approach of the solution phase reactant to the bioactive species. In addition, physical bulk, electrostatic repulsion, or inappropriate positioning of the bioactive species may also contribute to reduced efficiency of the immobilized bioactive species. Accordingly, it may be desirable to place one or more additional compounds as a "spacer" or "tether" between the chemical functional groups of the biodegradable polymer and the bioactive species to increase the space between the polymer and the bioactive species. The covalent attachment of bioactive species onto the biodegradable polymer according to the present invention is generally reversible, i.e., the bioactive species are released from the biodegradable polymer in a controlled, or predictable, manner over time. In addition, spacers, or tethers, capable of selectively releasing immobilized bioactive species provide another degree of controlled release of bioactive species. Suitable compounds for use as cleavable tethers, or cleavable spacers, include, but are not limited to, polyhydroxyacids, polyanhydrides, polyamino acids, tartarates, cysteine-linkers such as Lomant's Reagent, for example, derivatives of ethylene glycol-bis-succinimidyl-succinate, succinic acid or succinic anhydride, diaminohexane, glyoxylic acid, short chain polyethylene glycol, and glycine, for example. Other means are crosslinking via imidocarbonates, carbonates, oxiranes, aziridine and active double bonds and halogens. The reactive functionalities which are available on the biologically active agent for covalently bonding to the chemically reactive group of the biodegradable polymer are primarily amino groups, carboxyl groups and thio groups. While any of these may be used as the target of the chemically reactive group on the biodegradable polymer, for the most part, bonds to amino groups will be employed, particularly with the formation of amide bonds. To form amide bonds, one may use as a chemically reactive group wide-variety of active carboxyl groups, particularly esters, where the hydroxyl moiety is physiologically acceptable at the levels required. While a number of different hydroxyl groups may be employed, the most convenient are N-hydroxysuccinimide (NHS), and N-hydroxy sulfosuccinimide (sulfo-NHS), although other alcohols may also be employed. In some cases, special reagents may be used, such as azido, diazo, carbodiimide anhydride, hydrazine, dialdehydes, thiol groups, or amnines to form amides, esters, imines, thioethers, disulfides, substituted amines, or the like.

Polymers may be attached to the N- and/or C-terminus of a polypeptide. If the biological agent is a multimer (e.g., a dimer, trimer, tetramer), polymers may be attached to one or both termini of one or more polypeptide chains. Polymers may also be inserted in a polypeptide, if such insertion does not significantly affect the activity of the polypeptide. In yet other embodiments, one or more polymers are attached to sidechains of amino acids within the polypeptide. For example, the polymer can be an oligosaccharide that is attached to an amino acid of an apyrase.

Conjugates comprising a biological agent and a biodegradable polymer can further be conjugated to one or more other moieties. For example, they may be linked to a label, e.g., to permit detection of the conjugates in vivo. The conjugates may also be linked to a targeting agent that will target the conjugate to the appropriate site within a subject. A targeting agent may be, e.g., an antibody. For example, when the biological agent is an apyrase, it may be desirable to target a conjugate comprising the apyrase to endothelial cells. This can be accomplished, e.g., by linking to the apyrase or to the polymer an antibody binding specifically to membrane antigens of endoplasmic cells. Other targeting agents are known in the art for targeting various sites. Targeting agents can be linked to either the biological agent or the polymer, as described herein or according to methods known in the art.

Determination of Biological Activity of Biological Agents and Conjugates Thereof The biological activity of biological agents, whether or not linked to a polymer, can be determined according to methods known in the art. Exemplary assays are set forth below.

Where the biological agent is an apyrase or derived from (e.g., a fragment), or homologous to, an apyrase, several assays can be used to determine the rate of catalysis of substrates by the apyrase. For example, nucleotidase activity can be determined by measuring the amount or inorganic phosphate released from nucleotide substrates using, e.g., the technique of Daly and Ertingshausen (Clin. Chem. 18:263 (1972)). In this method, the complex of inorganic phosphate with phosphor reagent (ammonium molybdate in the presence of sulfuric acid) produces an unreduced phosphomolybdate compound. The absorbance of this complex at 340 nm is directly proportional to the inorganic phosphorus concentration. The nucleotide can be added to a final concentration of 1 mM and incubated at 37° C. for 30 minutes. The reagent can then be stopped with 100 volumes of phosphor reagent, and the amount of phosphate released from the reaction can be quantitated using a calcium/phosphorus combined standard (Sigma). This assay is further described in Mulero et al. (1999) J. Biol. Chem. 274:20064.

Alternatively, hydrolysis of ADP or ATP can be measured by incubating a sample of apyrase, e.g., cell lysates of cells expressing an apyrase, with either 200 µM ADP or 200 µM ATP, and $Ca^{2+}$ or $Mg^{2+}$ dependent release of free phosphate is determined. Malachite green can be used to stop the reaction, and absorbance at 610 nm can be used to determine levels of phosphate against the standard curve of $KH_2PO_4$ as described, e.g., in Geladopoulos et al. (1991) Anal. Biochem. 192: 112 and in Kaczmarek et al. (1996) J. Biol. Chem. 271:33116.

ATPDase activity of intact cells can also be determined by measuring the hydrolysis of [$^{14}$C]ADP to AMP, as described, e.g., in Kaczmarek et al. (1996) J. Biol. Chem. 271:33116. Briefly, a sample of apyrase or monolayers of cells expressing an apyrase, e.g., cells transfected with an expression construct encoding an apyrase, and appropriate control cells are incubated with [$^{14}$C]ADP (50 µCi/reaction; DuPont NEN) and the products analyzed on thin layer chromatography (TLC) plates (Whatman Labroatory Division, Clifton, N.J.). The solvent system may comprise isobutyl alcohol: 1-pentanol: ethylene glycol monoethyl ether: NH4OH water at ratios 90:60:180:90:120. The seperated compounds can be scanned for radioactivity with a Phosphorimager (Molecular Dynamics, Sunnyvale, Calif.) and degradation of the [$^{14}$C]ADP can be determined by ImageQuant software according to the manufacturer's instructions (Kaczmarek et al. (1996) J. Biol. Chem. 271:33116).

Platelet aggregation assays can be conducted as follows. Blood is obtained from an apparently healthy human volunteer and anticoagulated with 0.1 volume 3.2% sodium citrate. Platelet rich plasma is then prepared by centrifugation of whole blood at 280×g for 15 minutes at 22° C. Platelet-rich plasma is the preincubated with cell membrane or a cell lysate containing apyrase or with soluble apyrase for 10 minutes at 37° C. in a siliconized glass cuvette containing a stirring bar, followed by stimulation with either ADP (5 µg/ml), or thrombin (0.1 unit/ml) (Chronolog Corp., Havertown, Pa.). Platelet aggregation can be recorded for at least 10 minutes with Blood Lumi-Aggregometer, e.g., model 560 (Chronolog Corp., Havertown, Pa.), which detects platelet shape change. Data can be expressed as the percentage of light transmission with platelet-poor plasma equal to 100%. Further details are provided in Kaczmarek et al. (1996) J. Biol. Chem. 271: 33116.

Cell lysates or membrane preparations, e.g., from cells expressing an apyrase, can be prepared, e.g., as described in Kaczmarek et al. (1996) J. Biol. Chem. 271:33116.

The angiostatic (angiogenesis inhibiting) activity of a protein can be determined, e.g., in a HUVEC-endothelial cell proliferation assay. The assay can be performed in a 96 well plate. Primary human umbilical cells (H ECs) are seeded to $3 \times 10^3$ cells per well in EGM medium (Clonetics)/20% FCS (fetal bovein serum) and incubated at 37° C. for 24 hr. The cells can then be starved in M199 medium (GIBCO BRL) containing 0.5% FCS (M199-0.5% FCS) for 48 hr at 37° C. 100 ng/ml FGF is added to the solution containing the protein to be tested, e.g., conditioned media or membrane fractions derived from transfected host cells. The medium is added to starved cells and incubated for 72 hr at 37° C. The cells are then radiolabeled by $^3$H-thymidine for 6 hr. Radiolabeled cells are washed with PBS and trypsinized for liquid scintillation counting. Results can be plotted using Kaleidograph software (Abelbeck Software). The extent of angiogenesis in a tissue, can be evaluated by a variety of methods, such as are described in U.S. Pat. No. 6,248,327, for detecting immature and nascent vessel structures by immunohistochemistry.

The efficacy of the modified apyrases can also be tested in vivo, e.g., in animal models. One model is the CD39 null mouse, that displays prolonged bleeding times and yet, paradoxically has a predisposition to thrombogenesis in vivo (Enjyoji et al. (Nature Med. 5:1010 (1999) and WO 00/23459). It has been shown that i.v. injection of apyrases correct the abnormal bleeding times of these mice (Enjoyji et al., supra). Accordingly, modified apyrases can be administered to these mice, and their bleeding time and/or clot production monitored relative to CD39 null mice that have not received modified apyrase.

Graft viability can be determined according to methods known in the art, e.g., using animals, e.g., nude mice.

Where the biological agent is not an apyrase, biological activity tests of the particular biological agent can be conducted as known in the art. Exemplary tests are set forth in U.S. Pat. No. 6,312,921.

Diseases that can be Treated with the Compounds of the Invention

The soluble apyrase conjugates provided by the invention can be used for treating any disease that can benefit from an increase in enzymatic activity. Exemplary diseases include those that can benefit from a modulation of circulating levels of nucleotides in the blood. Such diseases or conditions include those associated with abnormal platelet aggregation, cardiac function, immune responses (inflammation).

Briefly, platelets are anuceleate cell fragments that are released from large hematopoietic precursors named megakaryocytes. Platelets adhere to sites of vascular injury, are activated and release ADP and other signaling molecules. As a result, the ADP that was released causes the platelets to undergo a shape change from smooth discs to spiculated spheres, the fibrinogen receptor is activated and the platelets are caused to aggregate at the site of injury. Interactions between activated platelet surfaces and coagulation proteins result in thrombin generation, further platelet activation, and formation of an insoluble plug, also referred to as plaque. These effects are mediated by a platelet ADP receptor termed P2-receptor, that is antagonized by ATP.

Although platelet aggregation is a necessary physiological response to vascular injury by fulfilling essential roles in mediating effective and immediate control of bleeding, abnormal platelet reactivity can also cause undesirable conditions, such as thrombotic disorders, occlusive vascular disease, unstable angina, myocardial infarction, post-angioplasty stenosis, cerebral ischaemia, thrombotic stroke and a variety of inflammatory vascular disorders associated with organ and cell transplantation. Any condition resulting from excessive or inappropriate platelet aggregation or reactivity can be treated by administering a modified apyrase of the invention to a subject.

As further described herein, the modified apyrases of the invention degrade preferably ADP as opposed to ATP, and have a long half-life in blood. Accordingly, an effective dose of a modified apyrase can be administered to a subject, e.g., at the site of or in the vicinity of the site of vascular injury.

Examples of therapeutic uses for modified apyrases of the invention include the treatment of individuals who suffer from coronary artery disease or injury following myocardial infarction; unstable angina; atherosclerosis; preeclampsia; embolism; platelet-associated ischemic disorders including lung, coronary and cerebral ischemia; and the prevention of reocclusion following thrombosis, thrombotic disorders icluding coronary artery thrombosis, cerebral artery thrombosis, intracardiac thrombosis, peripheral artery thrombosis, venous thrombosis, cerebral artery thrombosis, intracardiac thrombosis, venous thrombosis and thrombosis and coagulophathies associated with exposure to a foreign or injured tissue surface, in combination with angioplasty, carotid endarterectomy, anastomosis of vascular grafts, and chronic cardiovascular devices such as in-dwelling catheters or shunts. The modified apyrases of the invention can also be used to treat individuals at high risk for thrombus and plaque formation or reformation (severe arteriosclerosis), and be used for inhibition of occlusion, reocclusion, stenosis and/or restenosis of blood vessels. Yet other individuals that benefit from a reduction of platelet aggregation include those at risk for advanced coronary artery disease; individuals that are or will be undergoing angioplasty procedures (e.g., balloon angioplasty, laser angioplasty, coronary angioplasty, coronary atherectomy and similar techniques); individuals undergoing surgery that has a high risk of thrombus formation (e.g., coronary bypass surgery, insertion of a prosthetic valve or vessel and the like); and individuals having, or at risk of having, deep venous thrombosis (DVT), pulmonary embolism (PE), transient ischemic attacks (TIAs) or other related conditions where arterial occlusion is the common underlying feature.

The modified apyrases of the invention can be used to prevent stroke and for treating patients experiencing stroke due to vascular occlusion. Other applications include the inhibition of microvascular thrombosis, postischemic cerebral blood flow improvement, redution of cerebral infarction volumes and neurological deficit without inducing intracerebral hemorrhage, in stroke.

In vivo experiments support a role of modified apyrases for preventing vascular occlusion and the consequences thereof. For example, a recombinant adenovirus encoding CD39 was used to infect rat aortae and rabbit femoral vessels following balloon-mediated denudation and injury. It was found that the injured vasculature in the rat aortae displayed dramatically less intimal hyperplasia and smooth muscle proliferation responses post-CD39 adenoviral infection relative to the negative control adenoviral exposed vessels (Robson et al. (2000) Emerging Therapeutic Targets 4:155). In a contrary manner, CD39 knock-out mice have a predisposition to thrombogenesis.

The modified apyrases of the invention can also be used to modulate angiogenesis. A role for NTPDase1 and phosphohydrolysis of extracellular nucleotides in the regulation of cellular infiltration and new vessel growth in a model of angiogenesis has been shown (Goepfert et al. (2001) Circulation 104:3109). Accordingly, angiogenesis is promoted with NTPDase1. NTPDase 1 may be useful for treating, e.g., ischemic peripheral vascular diseases.

Abnormal platelet reactivity has also been linked to a variety of inflammatory vascular disorders, e.g., associated with transplantation. Quiescent EC express ATPDase which exerts an important thromboregulatory function by hydrolyzing both ATP and ADP. It has been shown that ATPDase activity is rapidly lost from the surface of the EC following ischemia-reperfusion injury and during graft rejection. Providing a mechanism for restoration or augmentation of ATPDase activity would benefit patients with such injuries or surgeries. Accordingly, modified apyrases can be used to prolong graft survival, at least in part by preventing platelet thrombi and vascular inflammation. For example, infusion of soluble potato apyrase has been shown to abrogate platelet sequestration in cardiac grafts where NTPDase activity has been lost (Koyamada et al. Transplantation 62:1739 (1996)). It has also been shown that cardiac xenografts of CD39 null mice undergo rejection with more rapid vascular occlusion than the matched wild type organs when grafted to rats with normal circulating platelets (Imai et al. (1999) Mol. Med. 5:743). Overexpression of CD39 also significantly prolonged graft survival when compared with a negative control in a system involving vascularised guinea-pig (to rat) xenografts overexpressing CD39. Moreover, in this model, platelet sequestration was also markedly decreased and vascular integrity better preserved (Imai et al. (2000) Transplantation 70:864). Accordingly, the modified apyrases of the invention can be administered to a subject receiving a graft, e.g., an autologous, allogeneic, syngeneic or xenogeneic graft.

The invention also permits treatment of thrombotic complications associated with myocardial infarction, deep vein thrombosis following orthopedic surgery, transient ischemic attack, coronary artery bypass graft, percutaneous transluminal coronary angioplasty, acute promyelocytic leukemia, diabetes, multiple myelomas, septic shock, purpura fulminanas, adult respiratory distress syndrome, angina, or aortic valve or vascular prosthesis. The methods of the invention can also be used to treat inflammatory diseases, e.g., inflammatory bowel disease. For example, a subject developing thrombotic complications as a result of sepsis can be treated by administration of a conjugate comprising CD39 (NTPDase1).

Also within the invention are modified apyrases which stimulate platelet aggregation and augmnent hemostasis; modulate angiogenesis, and/or modulate immune responses. For example, the wild-type CD39L1 stimulates platelet aggregation by converting the competitive antagonist (ATP) of ADP receptors into the specific agonist. Accordingly, CD39L1 conjugates can be used in such embodiments. Such apyrases can also be used to repair blood vessels by promoting thrombus formation. Apyrases can regulate angiogenesis by sealing off blood vessels.

In situations in which the biological agent is not an apyrase, use of such conjugates are based on the identity of the biological agent. For example, if the biological agent is an interleukin, the conjugate containing an interleukin can be used, e.g., for stimulating lymphocyte activation and/or proliferation. If the biological agent is an interferon, a conjugate containing interferon can be used for treating multiple sclerosis.

Other Uses for the Agents of the Invention

Modified apyrases of the invention can also be used ex vivo, e.g., in blood or platelet stocks, where one desires to prevent platelet aggregation (see, e.g., U.S. Pat. No. 5,378,601). Apyrases have been reported as protecting platelets during storage (Mirowiec et al. (Transfusion 36:5 (1996)). Prevention of platelet aggregation may also be desirable when obtaining blood samples from individuals. Accordingly, modified apyrases could be added to blood samples. In certain embodiments, recipients of blood samples, or containers for storing blood or platelets may contain modified apyrases prior to receiving blood or platelets. A syringe containing modified apyrase is also contemplated.

Other ex vivo or in vitro uses for the modified apyrases include their use in pyrophosphate-based DNA sequencing methodologies such as those described by Ronaghi et al. (Science 281:336 (1998)).

Modified apyrases can also be used for screening for modulators, e.g., inhibitors of apyrases.

Methods of Administrating the Compounds of the Invention

The therapeutic methods of the invention generally comprise administering to a subject in need thereof, a pharmaceutically effective amount of a pharmaceutical complex comprising a biological agent, e.g., a modified apyrase. The conjugates of this invention may be administered to mammals, preferably humans, either alone or, preferably, in combination with pharmaceutically acceptable carriers, excipients or diluents, in a pharmaceutical composition, according to standard pharmaceutical practice. The conjugates can be administered orally or parenterally, including the intravenous, intramuscular, intraperitoneal, subcutaneous, rectal and topical routes of administration.

Toxicity and therapeutic efficacy of the conjugates can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Conjugates which exhibit large therapeutic indices are preferred. While conjugates that exhibit toxic side effects may be used, care should be taken to design a delivery system that targets such reagents to the site of affected tissue in order to minimize potential damage to normal cells and, thereby, reduce side effects.

Data obtained from cell culture assays and animal studies can be used in formulating a range of dosage for use in humans. The dosage of such reagents lies preferably within a range of circulating concentrations that include the $ED_{50}$ with little or no toxicity. The dosage may vary within this range depending upon the dosage form employed and the route of administration utilized. For any reagent used in the method of the invention, the therapeutically effective dose can be estimated initially from cell culture assays. A dose may be formulated in animal models to achieve a circulating plasma concentration range that includes the $IC_{50}$ (i.e., the concentration of the conjugate which achieves a half-maximal inhibition of symptoms) as determined in cell culture. Levels of conjugates in plasma may be measured, for example, by high performance liquid chromatography.

A conjugate of the invention is preferably administered parenterally, e.g., by injection, e.g., intravenous (i.v.), subcutaneous, or intramuscular injection. Accordingly, pharmaceutical compositions may be in the form of a sterile injectable aqueous solution. Among the acceptable vehicles and solvents that may be employed are water, Ringer's solution and isotonic sodium chloride solution.

Sterile injectable preparation may also be a sterile injectable oil-in-water microemulsion where the compound of the invention is dissolved in the oily phase. For example, the active ingredient may be first dissolved in a mixture of soybean oil and lecithin. The oil solution then introduced into a water and glycerol mixture and processed to form a microemulsion.

The conjugates of the invention may be delivered in a single dose or delivered in repeat doses. The preferred time for administration of the second and later doses will depend on the half-life of the conjugate. For example, a second dose could be administered 3 days, one week or one month after the first dose.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The conjugates of the invention can also be administered in a softgel, e.g., silica gel and solgel, which holds the conjugates inside and releases them over time.

In other embodiments, modified apyrases or other conjugates are administered by local delivery systems. Non-limiting examples of local delivery systems for use in the present invention include intravascular drug delivery catheters, wires, pharmacological stents and endoluminal paving.

In a preferred embodiment the compounds for use in the present invention are administered to a desired site, e.g., a site of vascular injury or plaque formation, by direct intravascular deposition using intravascular catheters. Catheter systems for use in the present invention, include, for example, pressure-driven catheters, diffusion catheters and mechanical catheters. See, e.g. Wolinsky & Thung, J. Am. Coll. Cardiol., 15:475-81 (1990); Goldman et al., Atherosclerosis, 65:215-25 (1987); Nabel et al., Science, 294, 1285-8 (1990); Fram et al., J Am. Coll. Cardiol., 23:1570-71 (1994); Riessen et al., Human Gene Ther., 4, 749-58 (1993); Fernandez-Ortiz et al., Circulation, 89:1518-22 (1994).

In one embodiment, the administration of conjugates may be by pressure-driven catheter systems, including for example, porous catheters; microporous catheters, for example, those made by Cordis Corporation; macroporous catheters; transport catheters, for example, those made by Cardiovascular Dynamics/Boston Scientific; channeled balloon catheters, for example, those made by Boston Scientific; and infusion sleeve catheters, for example, those made by LocalMed.

In a preferred embodiment the methods of the invention utilize a pressure driven based catheter that is an infusion sleeve catheter, an example of which is described by Moura et al, Circulation, 92: 2229-2305 (1995) and further described in U.S. Pat. No. 5,279,565. The infusion sleeve, an example of which is that produced by LocalMed, is designed to allow independent control of both the apposition of conjugates against the arterial wall and the drug delivery of the conjugates into the wall. The efficacy of drug delivery by an infusion sleeve on the arterial architecture of a vessel is a function of proximal delivery pressure. In one embodiment, the effect of proximal pressure on delivery of compounds used in the methods of the present invention by an infusion sleeve catheter can be determined in vitro by histological evaluation of the treated artery by known methods. In one non-limiting example, a proximal pressure of between about 50 to 200 psi may be used to deliver, by an infusion sleeve catheter, the compounds for use in the methods of the present invention, preferably, between about 100 to about 150 psi, and most preferably, between about 50 to 100 psi.

In another embodiment, the compounds of the invention may be administered locally by diffusion-based catheter systems, including for example, double balloon, dispatch, hydrogel and coated stent catheters. Such methods are described in, e.g., U.S. Pat. No. 6,179,817. The methods of the invention also include local administration of the conjugates by mechanical device-based catheter systems, including for example, iontophoretic balloon catheters.

In another embodiment, conjugates are delivered to a site in an individual using coated medical devices, e.g., a coated stent.

The ability to locally deliver the compounds used in the present invention may be evaluated in vivo using known animal models, including for example, acute canine coronary models. For example, a compound for use in the methods of the present invention is administered by local delivery to a canine at a site of injury. The canine is sacrificed and then examined by known methods, including, for example, fluorescence microscopy.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In other embodiments, pharmaceutical compositions are administered orally or topically according to methods known in the art.

The conjugates of the invention may also be co-administered with other well known therapeutic agents that are selected for their particular usefulness against the condition that is being treated. The conjugates may be administered simultaneously or sequentially.

For example, modified apyrases can also be administered together with one or more other agents, e.g., antiplatelet agents, such as aspirin or GPIIb/IIIa-antagonists), direct antithrombin modalities (e.g., heparin) or certain fibrinolytic interventions. The agents of the invention can also be coadministered with an angiogenesis inhibitors, in which case the angiogenesis inhibitor is typically administered during or after chemotherapy, although it is preferably to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the angiogenesis inhibition methods after surgery where solid tumors have been removed as a prophylaxis against metastases.

In addition, since adenosine is the ultimate product of the degradation of ATP and ADP, and it is a major factor in mediating vasodilation by ATP, it may be preferable, in certain embodiments, to administer to a subject a modified apyrase and an agent that blocks adenosine receptors.

When a composition according to this invention is administered into a human subject, the daily dosage will normally be determined by the prescribing physician with the dosage generally varying according to the age, weight, and response of the individual patient, as well as the severity of the patient's symptoms.

Kits of the Invention

In one embodiment, a conjugate of the invention, and materials and/or reagents required for administering the complexes of the invention may be assembled together in a kit. When the components of the kit are provided in one or more liquid solutions, the liquid solution preferably is an aqueous solution, with a sterile aqueous solution being particularly preferred.

The kit may further comprise one or more other conjugates of the invention or other drug, e.g., an anti-platelet aggregating agent. These normally will be a separate formulation, but may be formulated into a single pharmaceutically acceptable composition. The container means may itself be geared for administration, such as a syringe, pipette, eye dropper, or other such like apparatus.

The compositions of these kits also may be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the agent.

The kits of the present invention may include a means for containing the vials in close confinement for commercial sale such as, e.g., injection or blow-molded plastic containers into which the desired vials are retained. Irrespective of the number or type of containers, the kits of the invention also may comprise, or be packaged with a separate instrument for assisting with the injection/administration or placement of the conjugate within the body of an animal. Such an instrument may be a syringe, an inhalant, pipette, forceps, measured spoon, eye dropper or any such medically approved delivery vehicle. Other instrumentation includes devices that permit the reading or monitoring of reactions, e.g., by the conjugates, or for determining the amounts of conjugates.

The present invention is further illustrated by the following examples which should not be construed as limiting in any way. The contents of all cited references (including literature references, issued patents, published patent applications as cited throughout this application) are hereby expressly incorporated by reference.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXEMPLIFICATION

Example 1

Formation of Aldehyde-Containing Polymer by Polysaccharide Oxidation

Dextran (MW=485 kDa), 22.5 g was dissolved in 500 mL water. Sodium periodate, 57 g, was dissolved in 200 mL of water and mixed with the dextran solution at 25° C. After 8 hours of incubation, the high-molecular components were extracted from the reaction mixture by flow dialysis, using a hollow fiber Amicon™ cartridge with a 10 kDa cutoff. The reaction mixture was concentrated to 200 mL, then a 10 fold volume of water (2 liters) was passed through. A forty mL aliquot of the reaction mixture was lyophilized to yield 1.81 g of product. The resultant polymer was slowly soluble in water at neutral and low pH and readily dissolved at pH>7 and remained soluble after pH adjustment to pH<7. Ten milligrams of the polymer were dissolved in deuterium oxide and a proton NMR was obtained.

Example 2

Formation of Polyalcohol by Reduction of Aldehyde-Containing Polymer

Sodium borohydride, 20 g, was dissolved in 20 mL water and mixed with 160 mL of 4.5% solution of the aldehyde containing polymer from Example 1. After 2 hours of incubation, the pH was adjusted to 6. Twenty minutes later, high molecular components were extracted by flow dialysis (as described in Example 1) and separated into two fractions using an Amicon cartridge with a 100 kDa cutoff. Both fractions were lyophilized. Yields: low molecular weight fractions: 2.4 g; high molecular weight fraction: 3.1 g. Ten milligrams of low molecular weight polymer were dissolved in 1 mL of deutero DMSO and proton NMR were obtained. FIG. 2 is a $^{13}C$ NMR of the polyacetal, dissolved in deuterium oxide which demonstrates carbons functionalized by alcohol functionality in the biodegradable biocompatible polyacetal.

Example 3

Preparation of Apyrase

The apyrase used in the examples was a purified form of potato apyrase. The apyrase was purchased from Aldrich-Sigma (apyrase grade VII, cat.# A6535). The apyrase has an activity over 200 units/mg. One unit refers to the amount of apyrase that liberates 1.0 µmole of inorganic phosphate (Pi) from ATP or ADP per minute at pH 6.5 at 30° C. This preparation has a low ATPase/ADPase ratio. The apyrase was further purified as follows.

Purified apyrase was purified in the native conformation by the Cibacron Blue column procedure. Potato apyrase eluted as a single peak of active enzyme (950 units/ml of ADPase activity) in the last step of Cibacron Blue affinity chromatography, as described in Kettlun et al. (1982) Phytochemistry 21:551. Protein from the active peak was analyzed by sodium dodecyl sulfate-polyacrylamide gel electrophoresis followed by electroblotting onto PVDF membranes (Millipore). The membrane was stained with Ponceau S, and a single band of 49 kDa was observed.

Example 4

Conjugation of Poly(hydroxymethylethylene hydroxymethylacetal) (PHF) to Apyrase

PHF prepared in Example 2 was succinylated with succinic anhydride in dimethylformamide. The succinilation was performed under argon, at 21° C. for 12 hours, at 5% PHF (w/w). Succinic anyhdride was added at 1:5 to PHF monomer (mole/mole). The reaction mixture was dried in vacuum. Then, the product was dissolved in water (5% w/w), desalted on Sephadex G-25, and lyophilized. Succinylation degree, as determined by titration, was 20±1% (0.2 carboxyl groups per monomer unit). The ayrase enzyme, obtained as described in Example 3, was dissolved in 50 mM PBS, pH=8, at 5 mg/ml, modified with FITC (1% w/w to protein), and purified on Sephadex G-25. The FITC labeled enzyme was conjugated with succinyl-PHF in the presence of ethyl-(dimethylamino-propyl)-carbodiimide (EDC) in 50 mM PBS, at protein concentration of 1 mg/ml and succinyl-PHF concentration 50 mg/ml. The reaction mixture was monitored by SEC HPLC. When conjugation degree reached about 95%, half of the reaction mixture was transferred to a separate vessel and further reacted with ethylenediamine (10:1 excess, EDC 1.5:1 to carboxyl groups) to obtain a positively charged conjugate. Both conjugates were purified on Sephadex G-25. SEC HPLC showed >95% conjugation with formation of conjugates nearly equal in hydrodynamic size to the original succinyl-PHF.

Example 5

Conjugated Apyrase Exhibits a Stronger Enzymatic Activity in vitro Relative to Unconjugated Apyrase The in vitro rate of hydrolysis of ATP and ADP by apyrase, unlinked to any polymer or linked to a positively charged PHF or a negatively charged PHF, was determined as follows. Aliquots of apyrase were incubated with either 200 µM ADP or 200 µM ATP, and $Ca^{2+}$ or $Mg^{2+}$ dependent release of free phosphate was determined. Malachite green was added to stop the reaction, and absorbance was measured at 610 nm to determine levels of phosphate generation against the standard curve of $KH_2PO_4$, as described in Kaczmarek et al. (1996) J. Biol. Chem. 271:33116 and Geladopoulos et al. (1991) Anal. Biochem. 192:112.

The results are set forth in Table 1.

TABLE 1

Rate of ATP and ADP breakdown of apyrase III or VII vs. positively and negatively charged apyrase conjugates

| | mg/ml | ATPase (nanomol Pi/min/mg) | ADPase (nanomol Pi/min/mg) | ATP/ADP |
|---|---|---|---|---|
| Unconjugated* | 2 | 82466 | 13932 | 5.9 |
| Conjugate + | 0.5 | 9,074 | 11,621 | 0.8 |
| Conjugate − | 0.5 | 15,350 | 23,205 | 0.7 |

*These data were obtained in a separate experiment relative to the data listed in the next two lines of the table.

The results indicate that the apyrase linked to a negatively or positively charged polymer is much more effective in degrading ADP than the non-conjugated apyrase is. Furthermore, the conjugates are much less effective in hydrolyzing ATP than the non-conjugated apyrase is. Thus, whereas the non-conjugated apyrase is 5.9 times more efficient in hydrolyzing ATP than ADP, the apyrase conjugated to a negatively or positively charged polymer hydrolyzes ADP more efficiently than ATP (ATP/ADP breakdown rate of more than 1 versus less than 1, respectively). As it is the abundance of ADP that is thought to lead to abnormal platelet aggregation and the diseases associated with that condition, the higher consumption rate of ADP relative to ATP of the charged conjugated apyrase will keep the level of ADP down more effectively than the free apyrase.

Example 6

Figure 3:
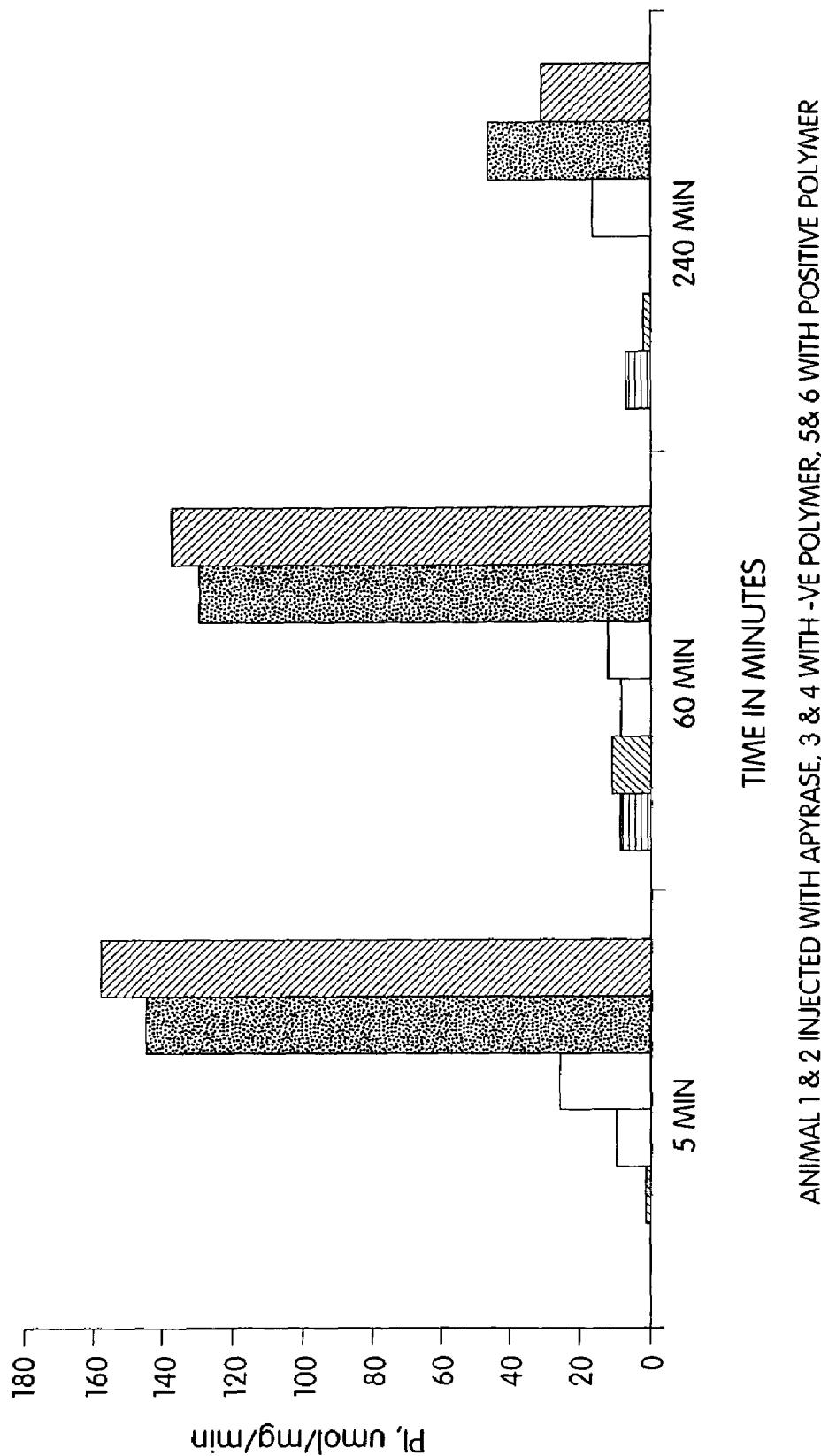
FIG. 3 depicts the levels of NTPDase present in the blood of mice injected with apyrase or apyrase conjugated to a positively or negatively charged polyacetal 5, 60 and 240 minutes after the injection.

Conjugated Apyrase Exhibits a Stronger Enzymatic Activity and Longer Half-life in vivo Relative to Unconjugated Apyrase In this experiment, the pharmacokinetic effects of conjugating an apyrase to a polymer were analyzed in an animal. The in vivo rate of hydrolysis of ATP and ADP by apyrase, unlinked to any polymer or linked to a positively charged PHF or a negatively charged PHF, was determined as follows. Mice were injected with 5 units unconjugated apyrase and approximately 1 unit of conjugated apyrase, mice were sacrificed after 5, 60 or 240 minutes, and the activity of apyrase in the mice was determined as described in Example 5 on samples of the animals' blood. The results, in Pi μmol/mg/min, are shown in Table 2 and in FIG. 3.

TABLE 2

Free and modified apyrase activities in nanomol/minute/ml blood (normalized)

|  | 5 minutes | 60 minutes | 240 minutes |
| --- | --- | --- | --- |
| unconjugated apyrase | 0 | 1 | 1 |
| Conjugate + | 4,449 | 3,857 | 1,102 |
| Conjugate − | 73 | 191 | 23 |

The results show the activities of free apyrase (i.e., not conjugated to a polymer) versus negatively and positively charged conjugated apyrase and the marked increase at different time intervals in activity of the conjugated apyrase over the free apyrase.

The results also indicate that the positively charged conjugate is more active than the negatively charged conjugate in the in vivo assay, which is the opposite from that which was observed in the in vitro assays. Without wanting to be limited to a particular mechanism of action, it is believed that positively charged conjugates are more active in vivo, since they are sequestered in vivo to the negatively charged endothelium.

Thus, the results indicate that apyrase conjugated to a polymer is more active in degrading ADP relative to ATP, and has a much longer half-life in vivo.

Equivalents

Those skilled in the art will recognize, or be able to ascertain using no more than routine experimentation, many equivalents to the specific embodiments of the invention described herein.

We claim:

1. A conjugate comprising an enzyme, which is covalently linked to a biodegradable polymer via a succinyl tether between the enzyme and the biodegradable polymer, wherein the biodegradable polymer is a polyacetal, and wherein the polyacetal is poly(hydroxymethylethylene hydroxymethylacetal).

2. The conjugate of claim 1, wherein the biodegradable polymer is negatively charged.

3. The conjugate of claim 1, wherein the biodegradable polymer is positively charged.

4. The conjugate of claim 1, wherein the biodegradable polymer has a molecular weight from about 2 kDa to about 250 kDa.

5. The conjugate of claim 3, wherein the biodegradable polymer has a molecular weight from about 20 kDa to about 100 kDa.

6. The conjugate of claim 1, further comprising a targeting agent.

7. The conjugate of claim 1, wherein the enzyme is an apyrase; the polyacetal is poly(hydroxymethylethylene hydroxymethylacetal); and the apyrase is a soluble form of CD39.

8. The conjugate of claim 7, wherein the apyrase comprises an amino acid sequence that is at least about 90% identical to SEQ ID NO: 2 and catalyzes hydrolysis of nucleoside diphosphates (NDPs).

9. The conjugate of claim 8, wherein the apyrase comprises the catalytic domain set forth in SEQ ID NO: 2.

10. A pharmaceutical preparation comprising a conjugate of claim 1 and a pharmaceutically acceptable carrier.

* * * * *

SEQUENCE LISTING

<160> NUMBER OF SEQ ID NOS: 7

<210> SEQ ID NO 1

<400> SEQUENCE: 1

000

<210> SEQ ID NO 2
<211> LENGTH: 510
<212> TYPE: PRT
<213> ORGANISM: Homo sapiens

<400> SEQUENCE: 2

Met Glu Asp Thr Lys Glu Ser Asn Val Lys Thr Phe Cys Ser Lys Asn
 1               5                  10                  15

Ile Leu Ala Ile Leu Gly Phe Ser Ser Ile Ile Ala Val Ile Ala Leu
                20                  25                  30

Leu Ala Val Gly Leu Thr Gln Asn Lys Ala Leu Pro Glu Asn Val Lys
            35                  40                  45

Tyr Gly Ile Val Leu Asp Ala Gly Ser Ser His Thr Ser Leu Tyr Ile
        50                  55                  60

Tyr Lys Trp Pro Ala Glu Lys Glu Asn Asp Thr Gly Val Val His Gln
    65                  70                  75                  80

Val Glu Glu Cys Arg Val Lys Gly Pro Gly Ile Ser Lys Phe Val Gln
                85                  90                  95

```
Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
            115                 120                 125

Gly Ala Thr Ala Gly Met Arg Leu Leu Arg Met Glu Ser Glu Glu Leu
130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Gly Ala
                165                 170                 175

Tyr Gly Trp Ile Thr Ile Asn Tyr Leu Leu Gly Lys Phe Ser Gln Lys
                180                 185                 190

Thr Arg Trp Phe Ser Ile Val Pro Tyr Glu Thr Asn Asn Gln Glu Thr
                195                 200                 205

Phe Gly Ala Leu Asp Leu Gly Gly Ala Ser Thr Gln Val Thr Phe Val
210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Val
                260                 265                 270

Ala Ser Asn Glu Ile Leu Arg Asp Pro Cys Phe His Pro Gly Tyr Lys
                275                 280                 285

Lys Val Val Asn Val Ser Asp Leu Tyr Lys Thr Pro Cys Thr Lys Arg
                290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
                340                 345                 350

Leu Gln Gly Asp Phe Gly Ala Phe Ser Ala Phe Tyr Phe Val Met Lys
                355                 360                 365

Phe Leu Asn Leu Thr Ser Glu Lys Val Ser Gln Glu Lys Val Thr Glu
                370                 375                 380

Met Met Lys Lys Phe Cys Ala Gln Pro Trp Glu Glu Ile Lys Thr Ser
385                 390                 395                 400

Tyr Ala Gly Val Lys Glu Lys Tyr Leu Ser Glu Tyr Cys Phe Ser Gly
                405                 410                 415

Thr Tyr Ile Leu Ser Leu Leu Leu Gln Gly Tyr His Phe Thr Ala Asp
                420                 425                 430

Ser Trp Glu His Ile His Phe Ile Gly Lys Ile Gln Gly Ser Asp Ala
                435                 440                 445

Gly Trp Thr Leu Gly Tyr Met Leu Asn Leu Thr Asn Met Ile Pro Ala
450                 455                 460

Glu Gln Pro Leu Ser Thr Pro Leu Ser His Ser Thr Tyr Val Phe Leu
465                 470                 475                 480

Met Val Leu Phe Ser Leu Val Leu Phe Thr Val Ala Ile Ile Gly Leu
                485                 490                 495

Leu Ile Phe His Lys Pro Ser Tyr Phe Trp Lys Asp Met Val
                500                 505                 510
```

```
<210> SEQ ID NO 3

<400> SEQUENCE: 3

000

<210> SEQ ID NO 4

<400> SEQUENCE: 4

000

<210> SEQ ID NO 5
<211> LENGTH: 8
<212> TYPE: PRT
<213> ORGANISM: Unknown Organism
<220> FEATURE:
<223> OTHER INFORMATION: Description of Unknown Organism: Amino acid
      sequence which is conserved among various apyrases
<220> FEATURE:
<221> NAME/KEY: MOD_RES
<222> LOCATION: (1)
<223> OTHER INFORMATION: Ile or Val
<220> FEATURE:
<221> NAME/KEY: MOD_RES
<222> LOCATION: (2)
<223> OTHER INFORMATION: Val, Met, or Ile
<220> FEATURE:
<221> NAME/KEY: MOD_RES
<222> LOCATION: (3)
<223> OTHER INFORMATION: Ile, Leu, Phe, or Cys
<220> FEATURE:
<221> NAME/KEY: MOD_RES
<222> LOCATION: (8)
<223> OTHER INFORMATION: Ser or Thr

<400> SEQUENCE: 5

Xaa Xaa Xaa Asp Ala Gly Ser Xaa
 1               5

<210> SEQ ID NO 6
<211> LENGTH: 7
<212> TYPE: PRT
<213> ORGANISM: Unknown Organism
<220> FEATURE:
<223> OTHER INFORMATION: Description of Unknown Organism: Amino acid
      sequence which shares strong homology between
      potato apyrase and pea NTPase

<400> SEQUENCE: 6

Pro Gly Leu Ser Ser Tyr Ala
 1               5

<210> SEQ ID NO 7
<211> LENGTH: 7
<212> TYPE: PRT
<213> ORGANISM: Unknown Organism
<220> FEATURE:
<223> OTHER INFORMATION: Description of Unknown Organism: Amino acid
      sequence which shares strong homology between
      potato apyrase and pea NTPase

<400> SEQUENCE: 7

Leu Tyr Val His Ser Tyr Leu
 1               5
```